(12) United States Patent
Martino et al.

(10) Patent No.: US 7,765,007 B2
(45) Date of Patent: *Jul. 27, 2010

(54) APPARATUS AND METHOD FOR PROVIDING CONTINENCE TO A GASTROINTESTINAL OSTOMY

(75) Inventors: Nicholas Martino, Fernandina Beach, FL (US); John Minasi, Amelia Island, FL (US); James G. Schneider, Chesterfield, MO (US)

(73) Assignee: Leto Medical, LLC, Fernandina, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/264,722

(22) Filed: Nov. 4, 2008

(65) Prior Publication Data

US 2009/0157140 A1 Jun. 18, 2009

Related U.S. Application Data

(63) Continuation of application No. 11/956,109, filed on Dec. 13, 2007.

(51) Int. Cl.
*A61N 1/18* (2006.01)
(52) U.S. Cl. .................................. 607/40; 607/41
(58) Field of Classification Search .................. None
See application file for complete search history.

(56) References Cited

U.S. PATENT DOCUMENTS

| | | | |
|---|---|---|---|
| 3,411,507 A | 11/1968 | Wingrove | |
| 3,952,726 A | 4/1976 | Hennig et al. | |
| 4,351,322 A | 9/1982 | Prager | |
| 4,981,465 A | 1/1991 | Ballan et al. | |
| 5,292,344 A | 3/1994 | Douglas | |
| 5,540,730 A | 7/1996 | Terry, Jr. et al. | |
| 5,569,216 A | 10/1996 | Kim | |
| 5,690,691 A | 11/1997 | Chen et al. | |
| 5,702,428 A | 12/1997 | Tippey et al. | |
| 5,995,872 A | 11/1999 | Bourgeois | |
| 6,026,326 A | 2/2000 | Bardy | |

(Continued)

FOREIGN PATENT DOCUMENTS

WO 03002193 A1 1/2003

(Continued)

OTHER PUBLICATIONS

PCT Search Report, PCT/US2008/083999 (Feb. 27, 2009).

(Continued)

*Primary Examiner*—Carl H. Layno
*Assistant Examiner*—Jon-Eric C. Morales
(74) *Attorney, Agent, or Firm*—Samuel Digirolamo; Husch Blackwell Sanders LLP

(57) ABSTRACT

An apparatus, and method, for providing continence to a gastrointestinal ostomy of a patient, the apparatus having a sealing device for retaining discharge of effluents or waste products from an ostomy, at least one pair of electrodes capable of delivering electrical stimulation to affect the smooth muscles of the patient's intestine and a stimulation generator in electrical communication with at least one pair of electrodes and capable of generating said electrical stimulation, wherein the electrical stimulation is selected to induce muscle contraction, relaxation, a tonic state or a flaccid state in the smooth muscles of the patient's intestine.

20 Claims, 20 Drawing Sheets

U.S. PATENT DOCUMENTS

| | | | |
|---|---|---|---|
| 6,033,390 A | 3/2000 | von Dyck | |
| 6,591,137 B1 | 7/2003 | Fischell et al. | |
| 6,606,518 B1 | 8/2003 | Cigaina | |
| 6,658,297 B2 | 12/2003 | Loch | |
| 6,659,936 B1 | 12/2003 | Furness et al. | |
| 6,689,111 B2 | 2/2004 | Mulhauser et al. | |
| 6,723,079 B2 | 4/2004 | Cline | |
| 6,915,165 B2 * | 7/2005 | Forsell | 607/40 |
| 7,120,497 B2 | 10/2006 | Ben-Haim et al. | |
| 7,221,978 B2 | 5/2007 | Ben-Haim et al. | |
| 7,343,201 B2 | 3/2008 | Mintchev | |
| 7,400,926 B2 | 7/2008 | Forsell | |
| 2003/0009221 A1 * | 1/2003 | Forsell | 623/14.13 |
| 2004/0093039 A1 | 5/2004 | Schumert | |
| 2006/0036293 A1 | 2/2006 | Whitehurst et al. | |
| 2006/0058576 A1 | 3/2006 | Davies et al. | |
| 2006/0058577 A1 | 3/2006 | Davies et al. | |
| 2006/0265021 A1 | 11/2006 | Herbert et al. | |
| 2007/0100303 A1 | 5/2007 | Gregory et al. | |
| 2007/0185541 A1 | 8/2007 | DiUbaldi et al. | |
| 2007/0191794 A1 | 8/2007 | Cline et al. | |

FOREIGN PATENT DOCUMENTS

| | | |
|---|---|---|
| WO | 2005051486 A1 | 6/2005 |
| WO | WO 2005051486 A1 * | 6/2005 |
| WO | 2005087312 A1 | 9/2005 |
| WO | 2007041795 A1 | 4/2007 |

OTHER PUBLICATIONS

PCT Written Opinion, PCT/US2008/083999 (Feb. 27, 2009).

* cited by examiner

APPARATUS AND METHOD FOR PROVIDING CONTINENCE TO A GASTROINTESTINAL OSTOMY

CROSS-REFERENCE TO RELATED APPLICATIONS

This application is a continuation in part of pending application Ser. No. 11/956,109 filed Dec. 13, 2007, which is hereby incorporated by reference in its entirety.

FIELD OF THE INVENTION

The present invention generally relates to continence devices, and more particularly, to an apparatus providing continence to a gastrointestinal ostomy, the apparatus utilizing a sealing device for retaining discharge of effluents or waste products from the ostomy in conjunction with an electrical stimulus generator to control muscle contraction and/or relaxation cycles of the intestinal muscles by directly stimulating the muscles or portions of the enteric nervous system or larger branch nerves of the autonomic nervous system associated with those muscles.

BACKGROUND OF THE INVENTION

An ostomy is a surgically-made opening in the body. Ostomies are available in a variety of types including, but not limited to, ileostomies, colostomies and urostomies, as may be needed by a particular patient. Although the discussion below will usually describe the invention with reference to the ostomy resulting from a colostomy procedure, it is to be understood that the invention can be applied to other types of ostomies as well. Further, although the discussion generally considers human patients, the structures described and claimed herein can be useful in non-human mammals as well.

A variety of medical conditions can lead to ostomy surgery, but the four most prevalent are colorectal cancer, diverticulitis, Crohn's Disease and ulcerative colitis. Ostomy surgery for these conditions generally requires the resection of the part or entire colon and/or rectum and the subsequent diversion of the colon or small bowel via an ostomy wherein the end of the remaining healthy portion of the colon or small bowel is brought through the abdominal wall, inverted on itself and sutured in place to form a stoma S. During inactive periods, the stomal tissue pulls together, rather like puckered lips. When waste is to be expelled, the tissue stretches to permit the waste to pass. Although it expands and contracts, the stoma does not have the firm muscle control of the anal sphincter. The muscles M of the remaining segment of colon remain intact and continue to function in a coordinated manner to effectively advance stools distally toward the stoma. However, while the colonic muscles remain relatively unaffected, the storage capacity naturally provided by the rectum and the muscle control provided by the anal sphincters are no longer available. Because of the loss of these key functions, the individual is rendered fecally incontinent (i.e., unable to control the time and place of waste evacuation) and must defecate into an ostomy bag for as long as they have the colostomy.

Fecal management in this manner is generally effective and is the current standard of care for individuals with colostomies. However, the use of ostomy bags often results in these individuals experiencing a variety of problems not ordinarily experienced by the general public (i.e., those with normal defecatory anatomy). These problems include leakage of intestinal gas, mucus, and waste, such as liquid and solid fecal material from around the stoma site. Such leakage not only causes unpleasant odors, but also leads to health problems, such as necrosis of the tissue surrounding the stoma site. The rate of leakage occurrence increases as the bag fills and the resulting weight pulls on the interface between the bag and the abdominal wall. Even when ostomy bags perform optimally, the fear of leakage, odor and the stigma associated with wearing the ostomy bag can have negative effects on the individual's quality of life, particularly their social and psychological well being.

The known art has made a variety of attempts to address these problems with various non-bag devices, without complete success. A number of barrier devices (e.g. foam plugs, catheter ports and inflatable sealing membranes) have been developed which essentially plug or seal the stoma until the user is ready to evacuate. To one degree or another, each of these devices was unable to maintain a safe and/or reliable seal with the intestinal lumen in which they resided, and resulted in leakage of waste around the device, device expulsion and/or tissue damage. Much of the lack of success of these devices can be attributed to the smooth muscle characteristics of the intestinal lumen. Generally, the nature of a smooth muscle lumen is to accommodate to any chronic bolus present within the lumen. In the case where the bolus is a stationary sealing structure, increases in the circumference of the intestinal lumen, as it accommodates, can contribute to leakage of luminal contents around the sealing structure.

To date, only one non-bag ostomy sealing device for the management of colostomies has been made commercially available. The Conseal® Plug made by Coloplast® is a tissue lumen sealing device having an adhesive base plate and a disposable foam plug which permits flatus to pass without the passage of feces, fluid or solid. The plug is supplied in a compressed state within a water-soluble film. The film disintegrates within a few seconds of insertion and the plug expands to its natural size to seal the stoma. The plug is removed to allow for fecal evacuation, after which a new plug is inserted. Although commercialized, the Conseal® Plug suffered from some of the short comings noted above specifically incidents of leakage and device expulsion.

The technical challenges faced in attempting to seal the gastrointestinal ostomy are better understood by reviewing the normal chemical, electrical and mechanical physiological mechanisms effecting colonic motility (i.e., the involuntary muscular activity of the colon which coordinates the movement of digesting materials towards the anus).

The Enteric Nervous System

The nervous system of the human body (and, for that matter, all mammals) has a profound influence on all digestive processes including colonic motility. Some of this control originates from connections between the central nervous system and the gastrointestinal tract, but just as importantly, the gastrointestinal tract is endowed with its own local nervous system, referred to as the enteric nervous system.

The principal components of the enteric nervous system are two networks or plexuses of neurons (the myenteric plexus and the submucosal plexus), both of which are embedded in the wall of the gastrointestinal tract. These enteric neurons secrete an array of chemical neurotransmitters that permit nerve signals to bridge the gap between nerve cells. Certain neurotransmitters are excitatory in nature, stimulating smooth muscle contractions, while others are inhibitory in nature, stimulating smooth muscle relaxation.

While the enteric nervous system can and does function autonomously, normal gastrointestinal function requires communication links between the enteric nervous system and the central nervous system. These links take the form of parasympathetic and sympathetic nerve fibers that connect either the central and enteric nervous systems or connect the central nervous system directly with the gastrointestinal tract. Through these cross connections, the gastrointestinal tract can provide sensory information to the central nervous system, and the central nervous system can affect gastrointestinal function. One example of the nervous interconnections within the gastrointestinal tract is the gastrocolic reflex, where distension of the stomach stimulates evacuation of the colon.

In general, parasympathetic nerve stimulation is excitatory in nature, causing contraction of gastrointestinal smooth muscle and increased gastrointestinal secretion and motor activity. Conversely, sympathetic nerve stimuli typically inhibit these activities.

Colonic Motility and Smooth Muscle

The colon is a dynamic luminal organ. A sectional view of the layers of the colon wall is provided in FIG. 20. Muscles located on the exterior of the colon run along the length thereof, extending and retracting the colon like a rubber band. These muscles contribute to a muscle action called haustral churning which facilitates mixing, fluid absorption and particle cohesion. Interior muscles wrap around the colon in circular bands that distend and contract the colon wall in an action that is similar to opening and closing a first. Working in concert, these muscles contribute to the principal type of motility called peristalsis (i.e., a distinctive pattern of smooth muscle contraction and relaxation that propels digesting materials distally toward the anus). Ultimately, the peristalsis advances stool into the rectum. When stool fills the rectum, the elastic quality of the wall permits the rectum to expand, creating a sac to accommodate stools just prior to defecation.

All muscles in the colon wall are smooth muscle which has properties distinctly different from skeletal muscle. Unlike skeletal muscle, smooth muscle is not under voluntary control. Smooth muscle fibers are arranged in intertwined, indistinct bundles, aligned in circular and longitudinal layers. Individual smooth muscle fibers are connected to neighboring smooth muscle cells by gap junctions, which allow these cells to be electrically coupled. The important consequence of this electrical coupling is that when an area of smooth muscle becomes depolarized, that depolarization spreads outward through adjacent sections of smooth muscle resulting in a well-coordinated contraction of, for example, an entire ring of circular smooth muscle of the colon.

Electrophysiology of Gastrointestinal Smooth Muscle

Normal gastrointestinal motility results from coordinated contractions of smooth muscle, which in turn derive from two basic patterns of electrical activity across the membranes of smooth muscle cells—slow waves and spike potentials.

Like other excitable cells, gastrointestinal smooth muscle cells maintain an electrical potential difference across their membranes. The resting membrane potential of smooth muscle cells is between −50 mV and −60 mV. In contrast to nerves and other types of muscle cells, the membrane potential of smooth muscle cells fluctuates spontaneously. Because the cells are electrically coupled, these fluctuations in membrane potential spread to adjacent sections of muscle, resulting in what are called "slow waves"—waves of partial depolarization in smooth muscle that sweep along the gastrointestinal tract for long distances. These partial depolarizations are equivalent to fluctuations in membrane potential of about five mV to fifteen mV. The frequency of slow waves depends on the section of the gastrointestinal tract. In the small intestine; they occur approximately 10 to 20 times per minute and in the large intestine about three to eight times per minute. Slow wave activity appears to be a property intrinsic to smooth muscle and dependent on nervous stimuli.

Importantly, slow waves are not action potentials and by themselves do not induce contractions. Rather, they coordinate muscle contractions in the gastrointestinal tract by controlling the appearance of a second type of depolarization event ("spike potentials"), which occurs only at the crests of slow waves. Spike potentials are true action potentials that induce muscle contraction. They result when a slow wave passes over an area of smooth muscle that has been primed by exposure to neurotransmitters released in their vicinity by neurons of the enteric nervous system. The neurotransmitters are released in response to a variety of local stimuli, including distension of the wall of the gastrointestinal tract and serve to "sensitize" the muscle by making its resting membrane potential more positive.

It is thus apparent how a particular pattern of motility is achieved. For example, when a large bolus (e.g., ingested food) enters the intestine the bolus distends the intestine, stretching its walls. Stretching stimulates nerves in the wall of the intestine to release neurotransmitters into smooth muscle at the site of distention—the membrane potential of that section of muscle becomes "more depolarized" or "less polarized". When a slow wave passes over the section of smooth muscle exposed to the neurotransmitters, spike potentials form and muscle contraction results. The contraction moves around and along the intestine in a coordinated manner because the muscle cells are electrically coupled through gap junctions. These coordinated muscle contractions work to mix and propel digesting materials distally.

Therefore, in view of the various shortcomings of the known art, the primary goal of the present invention is to overcome the loss of the normal physiological mechanisms associated with the anatomical derangements of a colostomy procedure, and in so doing, allow the individual to be effectively continent.

SUMMARY OF THE INVENTION

Accordingly, the invention is, briefly, an apparatus for providing continence to a gastrointestinal ostomy of a patient. The apparatus includes a sealing device for retaining discharge of effluents or waste products from the ostomy, at least one pair of electrodes capable of delivering electrical stimulation and at least one stimulation generator in selective communication with the at least one pair of electrodes. The at least one stimulation generator providing through any of the at least one pair of electrodes electrical stimulation to the patient's intestine, to thereby inhibit the advancement of intestinal contents by controlling muscle activity in a segment of the intestine. Generally, the electrical stimulus generator serves to inhibit the advancement of intestinal contents by controlling muscle activity in a segment of the intestine while the sealing device serves to retain the discharge of intestinal effluents or waste products not caused to be retained by the action of the stimulus generator (e.g., passive discharge from the ostomy due to gravity or intra-abdominal pressure).

The invention is also, briefly, a method for providing continence to a gastrointestinal ostomy of a patient. The method includes the steps of: providing a patient having a gastrointestinal ostomy with an apparatus for providing continence, the apparatus having a sealing device for retaining the discharge of intestinal effluents or waste products from the ostomy, at least one pair of electrodes capable of delivering electrical stimulation, at least one stimulation generator providing electrical stimulation to the patient's intestine through any of the at least one pair of electrodes; preselecting any of the at least one pair of electrodes and the site of the electrical stimulation; and applying electrical stimulation via the stimulation generator to the preselected at least one pair of electrodes there by inhibiting the discharge of intestinal effluents or waste products from the ostomy.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Throughout the drawings, like elements are indicated with like element numbers.

DETAILED DESCRIPTION OF THE PREFERRED EMBODIMENTS

Figure 1:
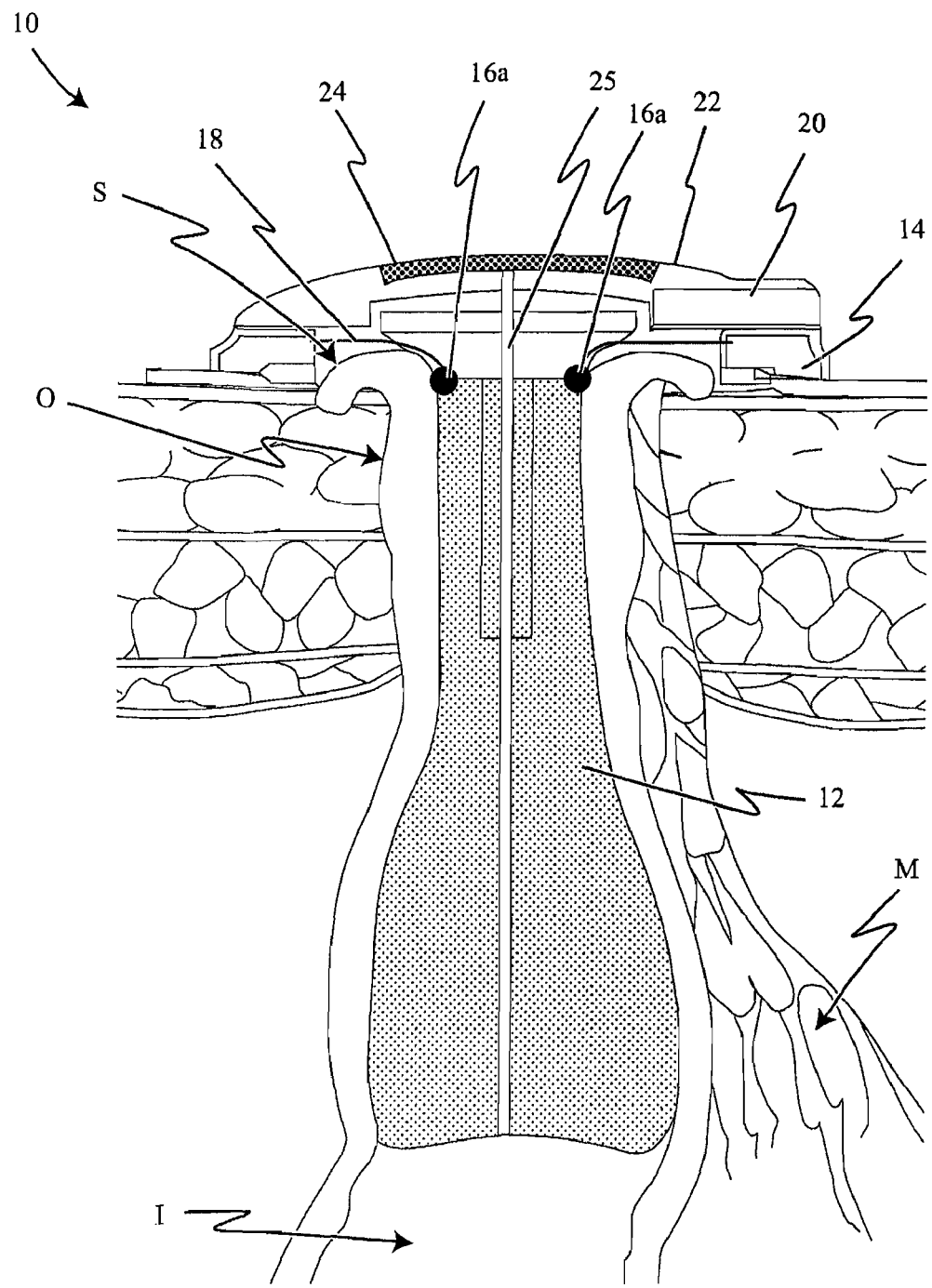
FIG. 1 is a longitudinal sectional view of an apparatus for providing continence, shown in place in an ostomy, the apparatus being constructed in accordance with and embodying the present invention and showing a plug type sealing device with a vent channel having electrodes incorporated therein and an external stimulus generator positioned peristomally and having electrodes connected thereto, the electrodes being located intraluminally to the intestinal wall.
Figure 2:
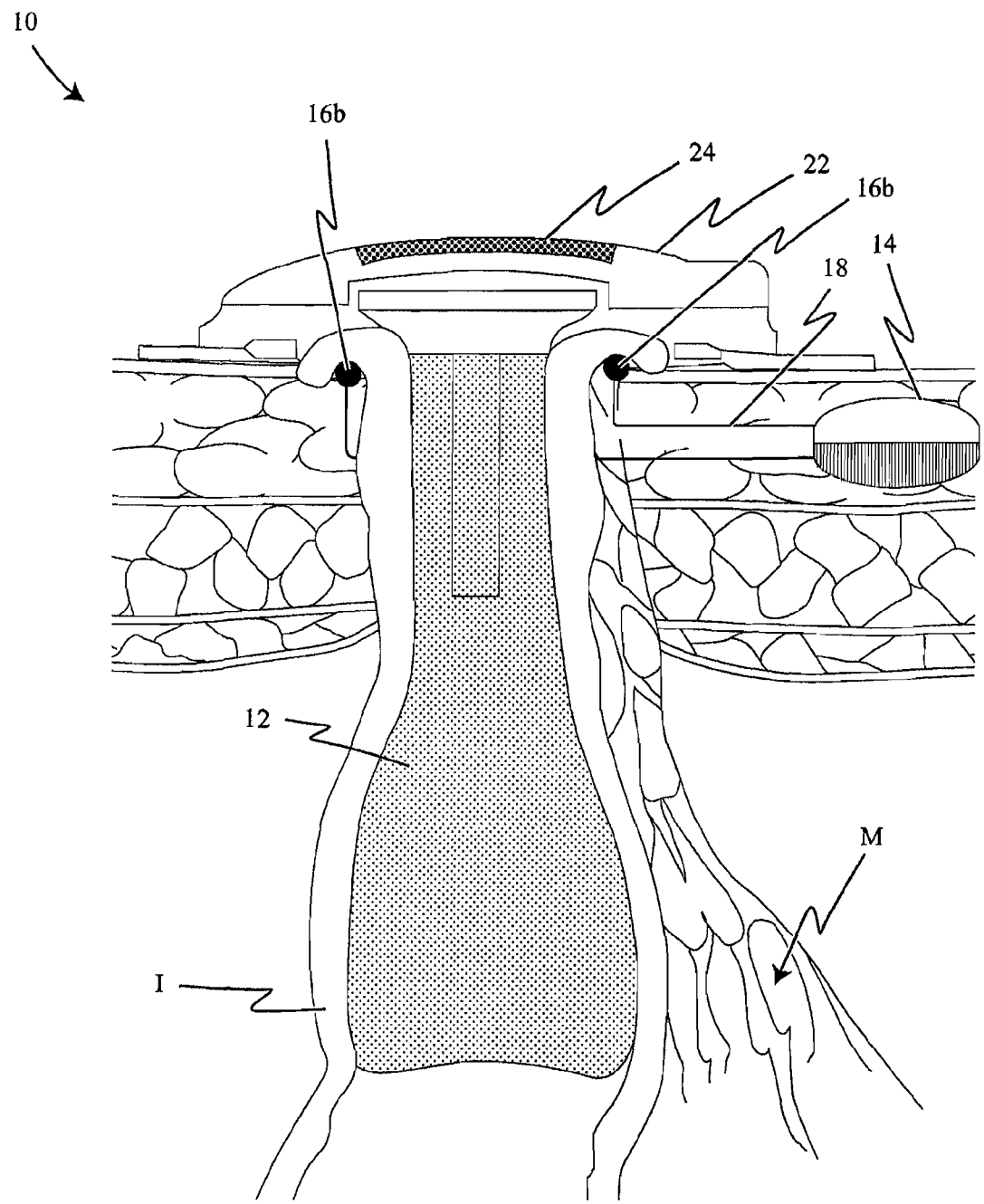
FIG. 2 is a longitudinal sectional view of an apparatus for providing continence, shown in place in an ostomy, the apparatus being constructed in accordance with and embodying the present invention and showing a plug type sealing device and a implantable stimulus generator having electrodes connected thereto, the electrodes being fixed extraluminally to the intestinal wall.
Figure 3:
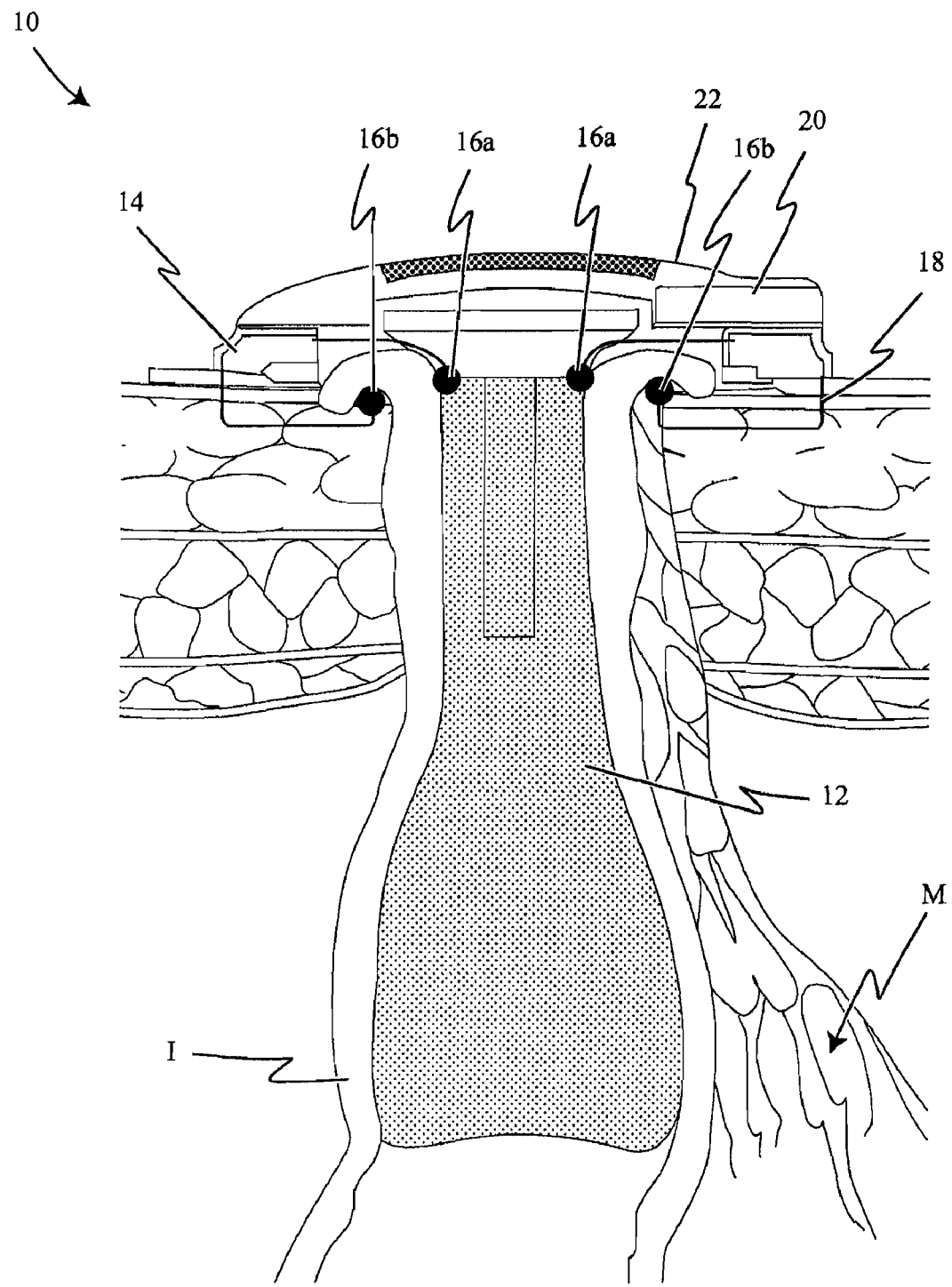
FIG. 3 is a longitudinal sectional view of an apparatus for providing continence, shown in place in an ostomy, the apparatus being constructed in accordance with and embodying the present invention and showing a plug type sealing device having electrodes incorporated therein and an external stimulus generator positioned peristomally and having electrodes connected thereto, the electrodes being located intraluminally as well as fixed extraluminally to the intestinal wall.

The following description of the preferred embodiment(s) is merely exemplary in nature and is in no way intended to limit the invention, its application, or uses.

In its basic form, the new apparatus for providing continence to a gastrointestinal ostomy, generally designated 10, includes a sealing device 12, and an electrical stimulus generator 14 in electrical communication with at least one pair of electrodes 16. All or part of apparatus 10 can be located inside the patient's body. Alternatively, all or part of apparatus 10 can be located outside the patient's body. For example, the sealing device may be located inside the patient's body, such as, a plug residing within the intestinal lumen, or alternatively, the sealing device may be located outside the patient's body, such as, an absorbent pad placed against the stoma. The stimulus generator may be located inside the patient's body, such as, implanted within the abdominal wall or cavity, or alternatively, the stimulus generator may be located outside the patient's body, such as, integrated into an exterior abdominal faceplate. The electrodes may be located inside the patient's body, such as, fixed to the intestinal muscles within the abdominal wall or cavity. Alternatively, the electrodes may be located outside the patient's body, such as, fixed to the stomal tissue.

The purpose of sealing device 12 is to retain the discharge of intestinal effluents or waste products not contained by the action of the stimulus generator, for example, passive discharge from the ostomy due to gravity or intra-abdominal pressure. For the purpose of the present invention, a sealing device is defined as any structure positioned internal and/or external to the patient's intestine, for the purpose of obstructing or containing discharge of intestinal effluent or waste from the ostomy.

In one group of embodiments, e.g. those shown in FIGS. 1-12 and 15-17, sealing device 12 is made of a generally non-absorbent, liquid-impermeable material, and the seal is accomplished by obstructing the discharge of effluents or waste products from the ostomy. Examples include plugs, catheters with removable plugs and stoma sealing membranes.

Figure 13:
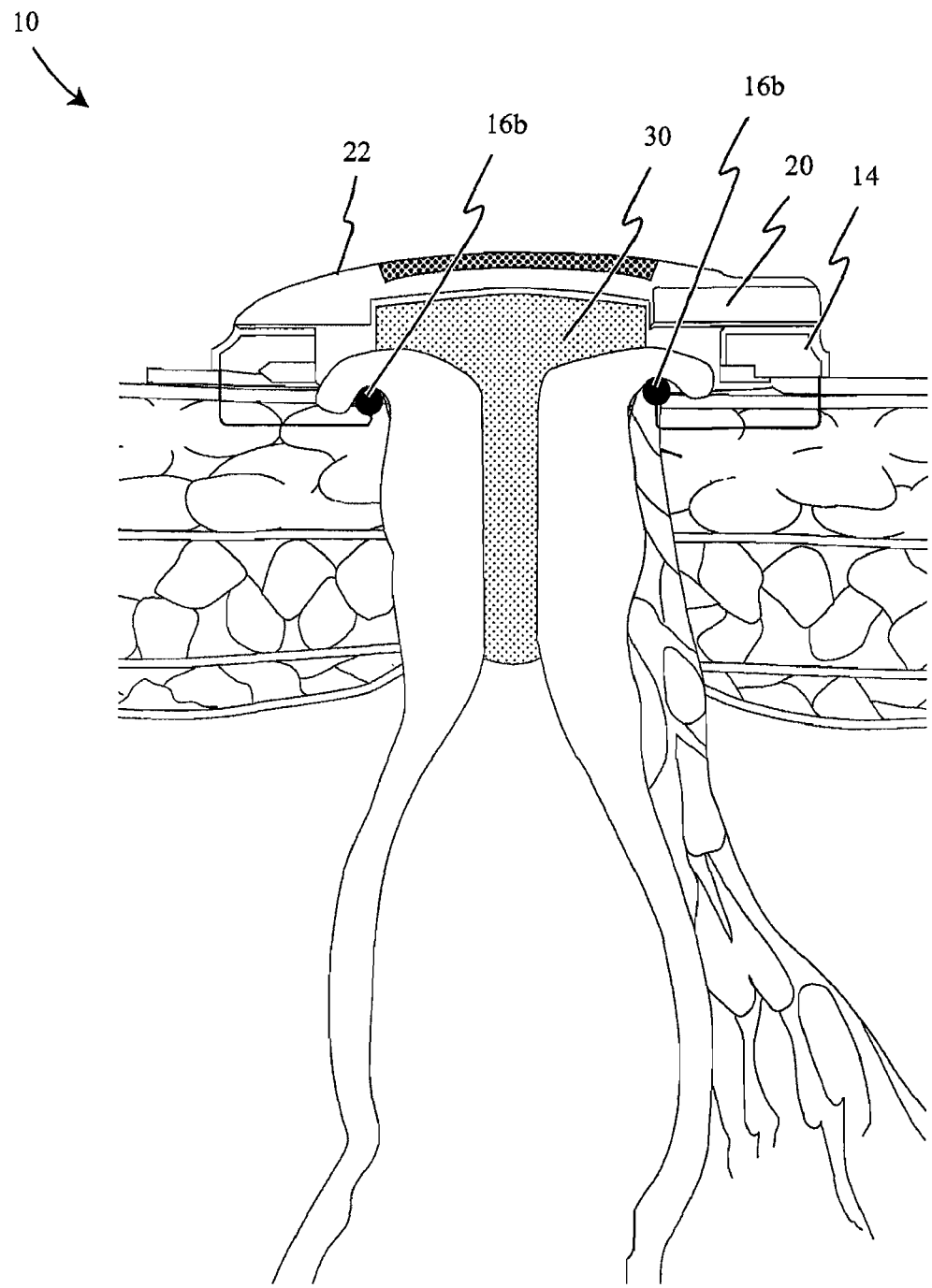
FIG. 13 is a longitudinal sectional view of an apparatus for providing continence, shown in place in an ostomy, the apparatus being constructed in accordance with and embodying the present invention and showing a tampon type sealing device and an external stimulus generator positioned peristomally and having electrodes connected thereto, the electrodes being fixed extraluminally to the intestinal wall.
Figure 14:
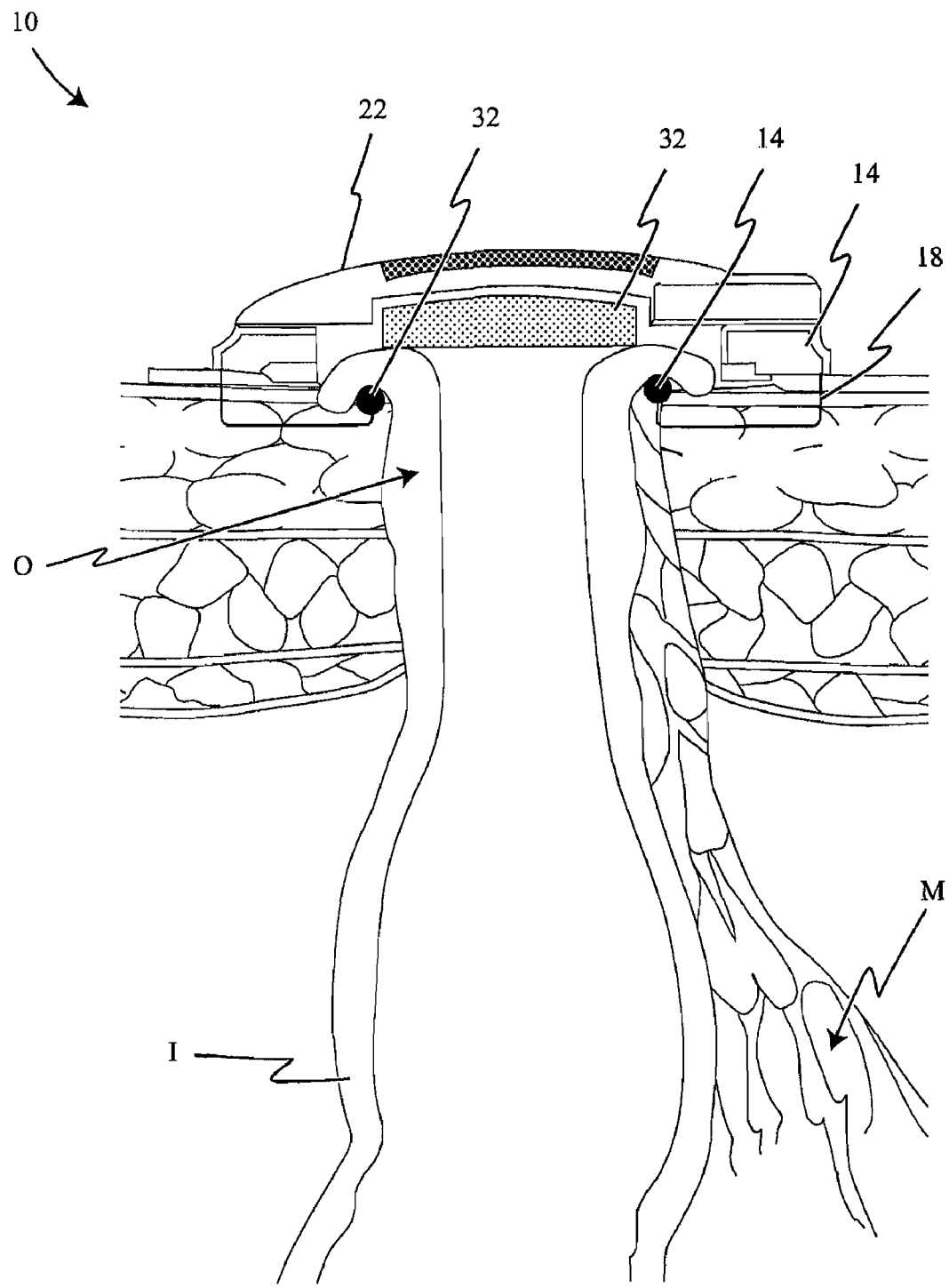
FIG. 14 is a longitudinal sectional view of an apparatus for providing continence, shown in place in an ostomy, the apparatus being constructed in accordance with and embodying the present invention and showing an absorbent pad type sealing device and an external stimulus generator positioned peristomally and having electrodes connected thereto, the electrodes being fixed extraluminally to the intestinal wall.

In another group of embodiments, the sealing device is an absorbent material, and the seal is accomplished by absorbing the discharge of effluents or waste products from the ostomy. Examples include tampons 30 or absorbent pads 32, as illustrated in FIGS. 13 and 14, respectively, for example.

Figure 18:
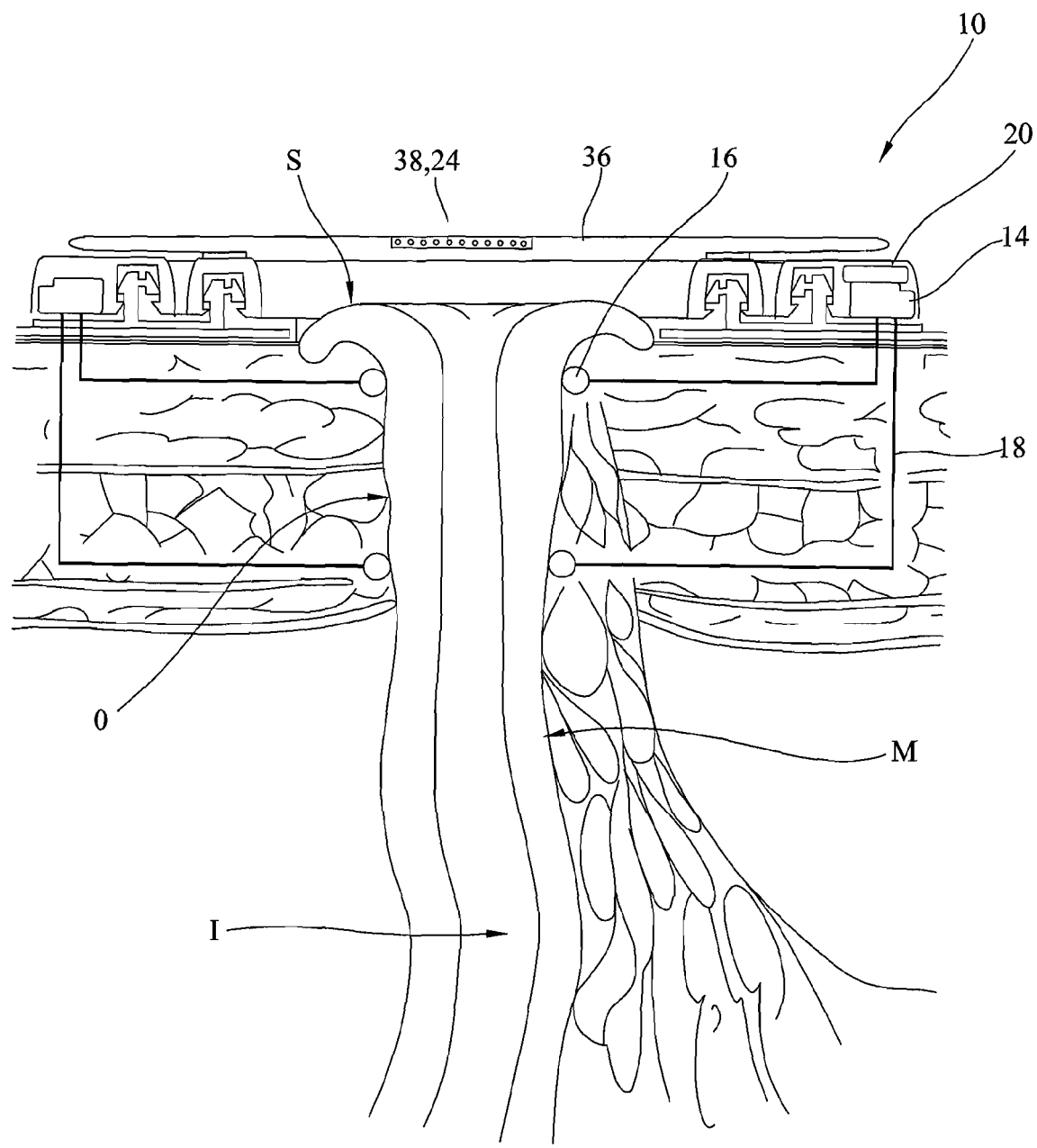
FIG. 18 is a longitudinal view of an apparatus for providing continence, shown in place in an ostomy, the apparatus being constructed in accordance with and embodying the present invention and showing a receptacle type sealing device and an external stimulus generator positioned peristomally and having electrodes connected thereto, the electrodes being fixed extraluminally to the intestinal wall.
Figure 19:
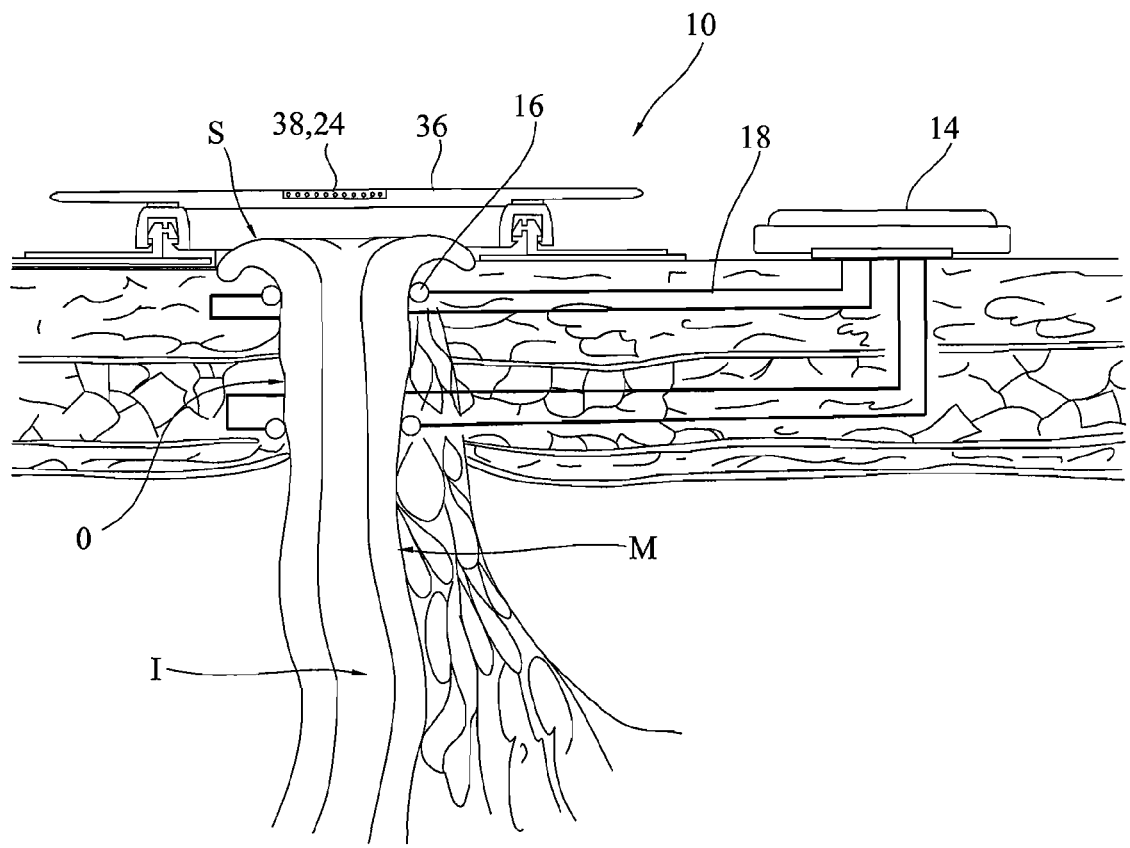
FIG. 19 is a longitudinal view of an apparatus for providing continence, shown in place in an ostomy, the apparatus being constructed in accordance with and embodying the present invention and showing a receptacle type sealing device and an external stimulus generator positioned non-peristomally and having electrodes connected thereto, the electrodes being fixed extraluminally to the intestinal wall.

In another group of embodiments, e.g., those shown in FIGS. 18 and 19, the sealing device is a receptacle, and the seal is accomplished by receiving and/or capturing the discharge of effluents or waste products from the ostomy. An example is an ostomy bag 36 which can vary in its size and capacity for retaining the discharge of effluents or waste products from the ostomy.

Generally, the sealing devices remain in place for the period of time continence is desired and are selectively removed for evacuation of the bowel of the patient. After which the sealing device is put back in place or disposed of and a new sealing device is placed. However, in the case of the catheter 26 with a removable plug 28, shown in FIG. 11, the catheter portion can remain indwelling and the plug separately removed for bowel evacuation. Plug 28 can then be re-inserted or disposed and replaced, if preferred.

If desired, apparatus 10 can incorporate a structure to vent flatus from the ostomy such as a venting channel 25, for example shown in FIG. 1, which allows flatus to pass through the a plug type sealing device 12. Alternatively, the sealing device 12 may have irregular surfaces such as protrusions, for example, which allow flatus to pass around the sealing device while still maintaining a seal with the mucosal wall of the intestine. In another example, a venting disc 38 can be incorporated into the wall of a receptacle type sealing device 36, as shown in FIG. 18, which allows flatus to escape from the sealing device. If desired, the apparatus 10 may also incorporate a deodorizing element 24, for example shown in FIG. 1, within cover 22 and above the distal end of sealing device 12 when cover 22 is in the closed position, or incorporated into the venting disc 38 as shown in FIG. 18 for example.

Electrical stimulus generator 14 can include a conventional electrical pulse generator (not seen), which, when activated, produces the desired electrical stimulus. The source of power for the stimulus generator can be, for example, a battery, such as that indicated at 20 in FIG. 1, located, for example, beneath a cover 22 over ostomy O and the distal end of plug style sealing device 12. The electrical stimulus is then conveyed to the target muscles M by leads 18 and electrodes 16.

Stimulus generator 14 can also have, in addition to the pulse generator, a known controller (not shown) that, if desired, can include a suitable programmable microprocessor of known or newly developed variety. The controller can direct the pulse generator in such a way that the pulse generator produces the desired stimulus, combination of stimuli, sequence of stimuli, and/or timing of stimuli. As an example, the electrical stimulation provided by the pulse generator can provide monophasic, biphasic or multiphasic waveform stimuli in known manner.

The stimulus generator 14 can also include circuitry that is capable of sensing an electrical, physical or chemical event, status or property, which would be input to the controller and result in the controller directing the pulse generator to deliver an appropriate electrical stimulation in response to sensing the event. This feedback mechanism will minimize power consumption as well as inadvertent reduction of the physiologic response to electrical stimulation, by delivering electrical stimulation only in response to a sensed event rather than delivering stimulation continuously or at a predetermined fixed rate. For example, generator 14 can be made to sense a change in impedance associated with a change in distance between two of the electrodes 16. In another example, generator 14 can be made to sense electrical depolarization activity across the membranes of smooth muscle cells, such as slow wave and spike potentials, and to then deliver the appropriate electrical stimulation to induce the desired contracted, relaxed, tonic or flaccid state in a segment of the intestine. In another example, generator 14 can be made to sense physical smooth muscle contraction and/or relaxation cycles by measuring the change in electrical resistance of a strain gauge fixed to the intestinal wall, and to then deliver the appropriate electrical stimulation in response. In another example, generator 14 can be made to sense a biochemical change such as an increase or decrease in neurotransmitter activity in smooth muscle cells, and to then deliver the appropriate electrical stimulation in response. In yet another example, generator 14 can be made to sense the status of the luminal contents. In one such example, a non-toxic substance can be ingested by the patient in an amount that results in a detectable concentration of the substance being present in the stool. In the case where the substance is electrically conductive, the generator will sense a change in electrical resistance between electrodes fixed to the intestinal wall, and will then deliver the appropriate electrical stimulation in response. The sensed event is generally sensed at a first location on the smooth muscles of the intestine or portions of the enteric nervous system or larger branch nerves N of the autonomic nervous system associated with those muscles. The invoked electrical stimulation is generally invoked at a second location on the smooth muscles of the intestine or portions of the enteric nervous system or larger branch nerves of the autonomic nervous system associated with those muscles. Alternatively, the sensing and electrical stimulation locations may be one in the same.

In another embodiment of the present invention, stimulus generator component 14 of apparatus 10 is implantable and optionally possesses an electrical coil or other structure for receiving energy and/or information in known manner. The coil receives power and/or data by inductive or radiofrequency coupling to a transmitting coil placed outside the body, thus avoiding the need for electrical wires to connect the stimulus generator 14 to a conventional external power source or controller (not shown). More specifically, the alternative stimulus generator 14 is foreseen as a wireless mechanism for receiving and/or transmitting signals (e.g., stimulation parameter signals) via telemetry and a wireless mechanism for receiving and/or storing electrical power within stimulus generator 14.

Figure 20:
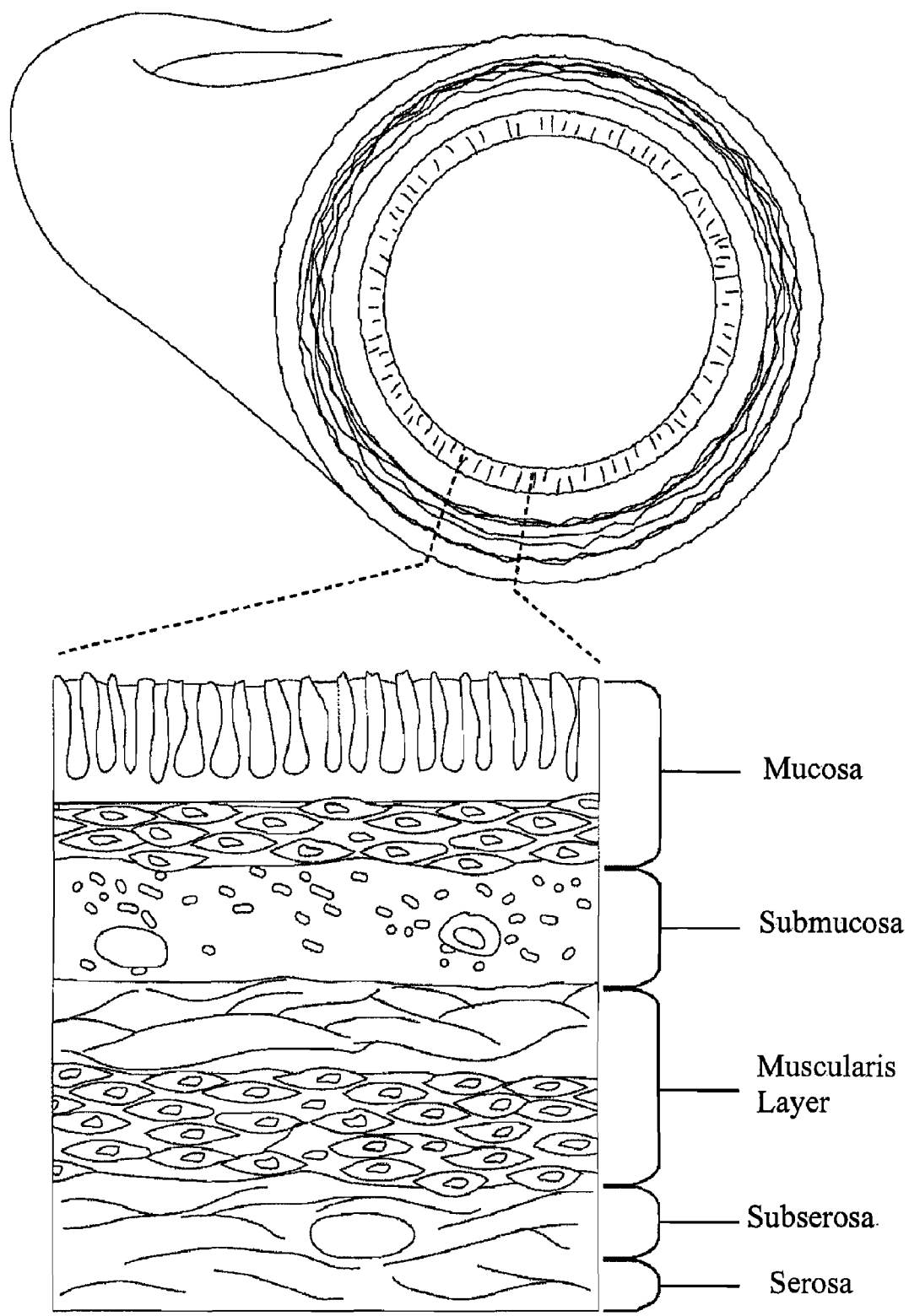
FIG. 20 is a sectional view of the layers of the colon wall.

The purpose of electrodes 16 is to; deliver electrical stimulation directly to, and/or, receive sensing signals indicative of an electrical, physical or chemical event, status or property from, the smooth muscles M of the intestine or portions of the enteric nervous system or larger branch nerves N of the autonomic nervous system associated with those muscles. If the muscles are to be stimulated or sensed directly, the electrodes can be disposed on the intestinal serosa, subserosa, mucosa, submucosa or muscularis layers (see FIG. 20). If a portion of the enteric nervous system or larger branch nerves of the autonomic nervous system are to be stimulated or sensed directly, the electrodes can be disposed in positions to deliver stimulation to, or receive sensing signals from, a portion of the autonomic nervous system including the parasympathetic and sympathetic nervous systems.

If only one pair of electrodes 16 is provided, all of the desired electrical stimuli can be sent to that single pair of electrodes. Alternatively, if at least two pairs of electrodes 16 are provided, the desired electrical stimuli can be sent sequentially to the multiple pairs of electrodes. It should be noted that "a pair of electrodes" can include one electrode being a conductive surface of the stimulus generator.

Figure 4:
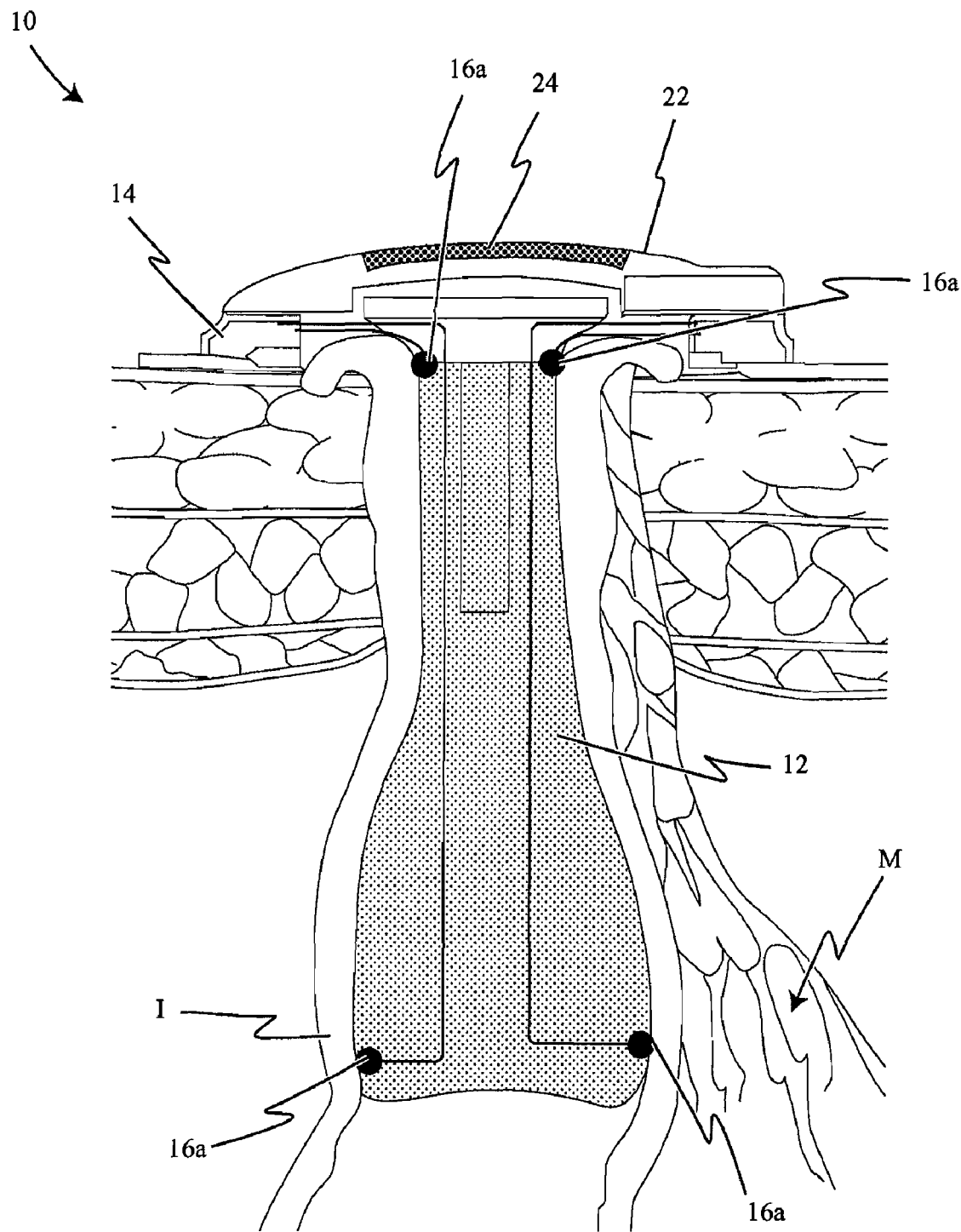
FIG. 4 is a longitudinal sectional view of an apparatus for providing continence, shown in place in an ostomy, the apparatus being constructed in accordance with and embodying the present invention and showing a plug type sealing device having multiple sets of electrodes incorporated therein and an external stimulus generator positioned peristomally and having electrodes connected thereto, the electrodes being located intraluminally to the intestinal wall.
Figure 5:
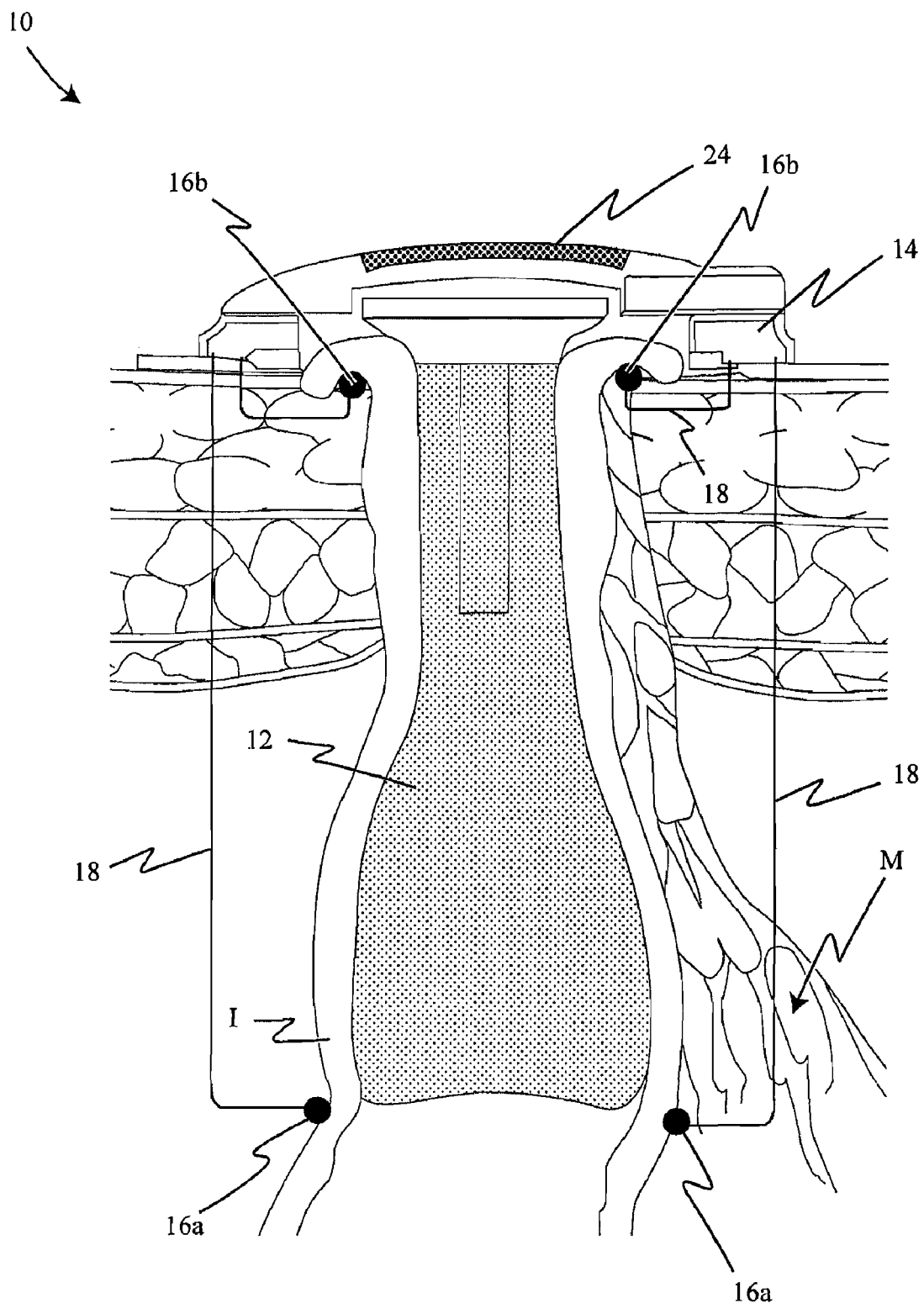
FIG. 5 is a longitudinal sectional view of an apparatus for providing continence, shown in place in an ostomy, the apparatus being constructed in accordance with and embodying the present invention and showing a plug type sealing device and an external stimulus generator positioned peristomally and having electrodes connected thereto, the electrodes being fixed extraluminally to the intestinal wall.
Figure 6:
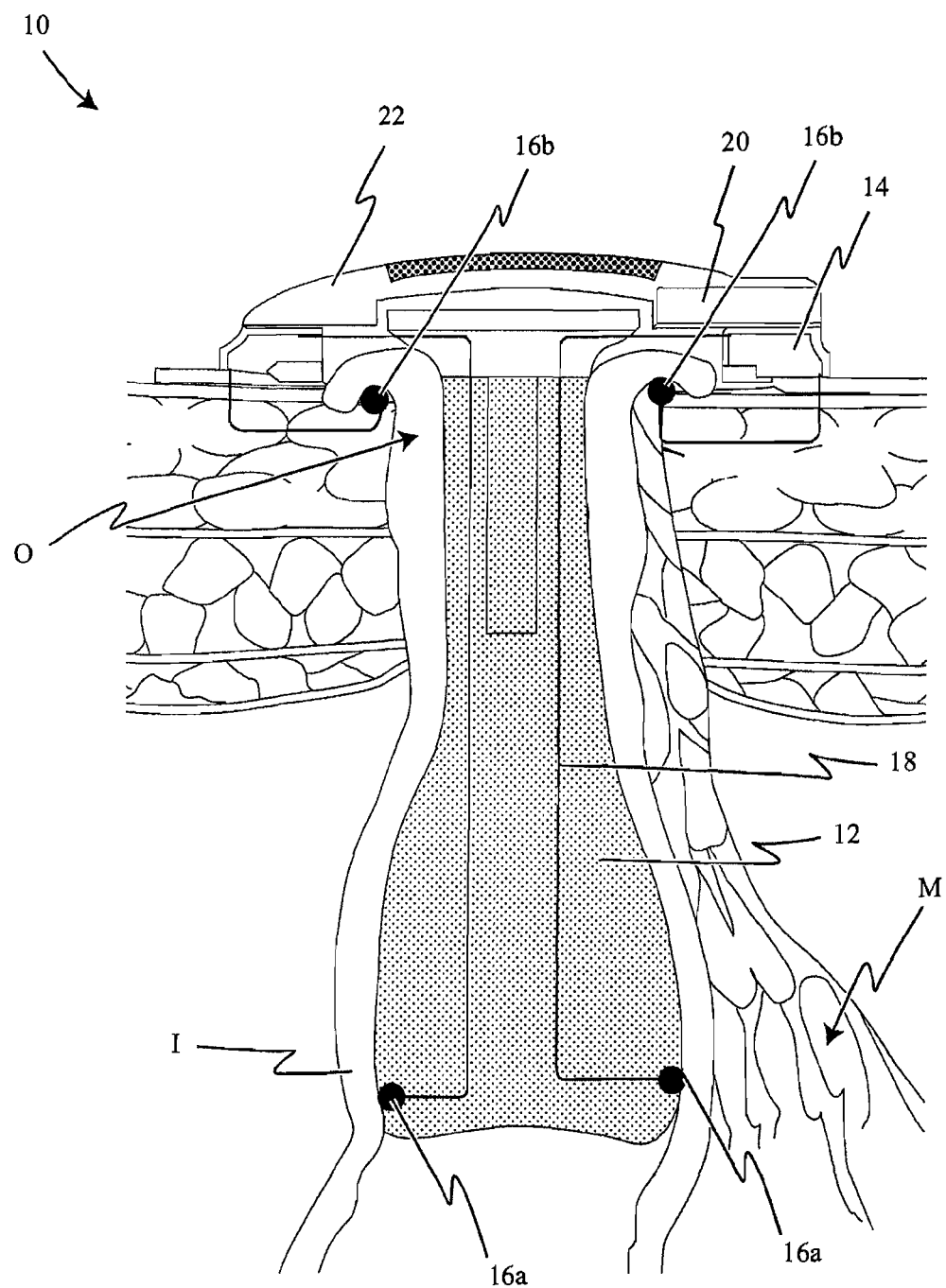
FIG. 6 is a longitudinal sectional view of an apparatus for providing continence, shown in place in an ostomy, the apparatus being constructed in accordance with and embodying the present invention and showing a plug type sealing device having electrodes incorporated therein and an external stimulus generator positioned peristomally and having electrodes connected thereto, the electrodes being located intraluminally as well as fixed extraluminally to the intestinal wall.
Figure 7:
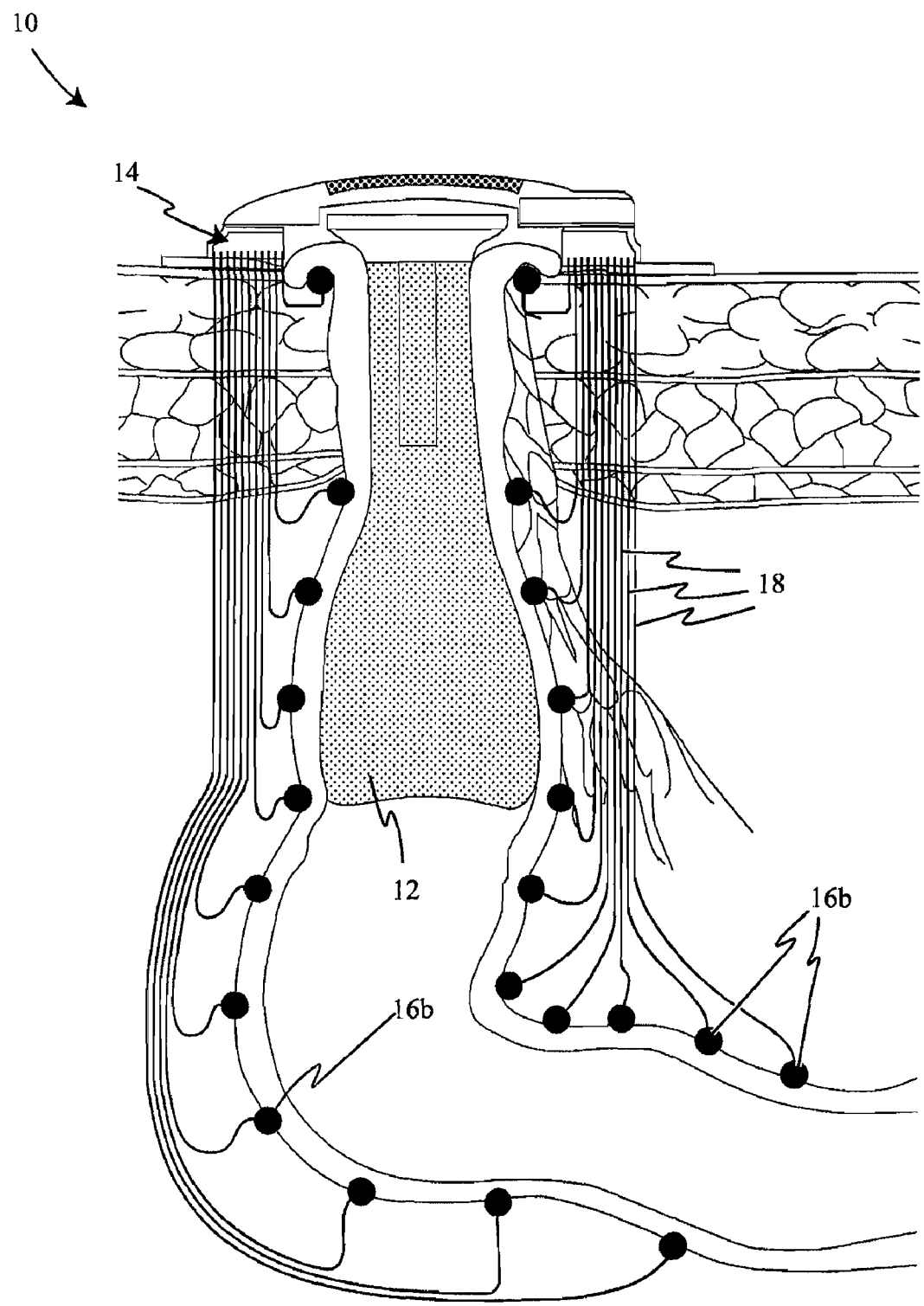
FIG. 7 is a longitudinal sectional view of an apparatus for providing continence in keeping with the embodiment of FIG. 5, but having many more electrode sets connected thereto.

In one group of embodiments, e.g. those shown in FIGS. 1 and 4, at least one set of electrodes 16*a* is incorporated into the lumen sealing structure 12 portion of apparatus 10. In another group of embodiments, e.g. those shown in FIGS. 2, 5, 7, 8, 9, 11, 12, 13, 14, 18 and 19, the at least one set of electrodes 16*a* is positioned very close/adjacent relative to the sealing structure but are not actually incorporated into the material of the sealing structure 12 of apparatus 10. In a further embodiment, e.g. those shown in FIGS. 3 and 6, a combination of electrodes 16*a* and 16*b* are used with apparatus 10. In the embodiment shown in FIG. 10, at least one set of electrodes 16*c* is fixed to the large branch nerves N of the autonomic nervous system.

Electrodes 16 have appropriate structure to permit them to be suitably anchored to the stimulation site (whether on the smooth muscle of the intestine or portions of the enteric nervous system or larger branch nerves of the autonomic nervous system associated with those muscles), in order to maintain electrical contact with the site. Examples include suturing, stapling, piercing, gluing or by direct contact force.

Electrodes 16 are preferably flexible rather than rigid, so as to conform to the stimulation site and thus not interfere with contractions and other movements of any portion of intestine I and not harm the stimulation site, or any adjacent organ. Also, electrodes 16 can be electrically attached to the lead in a variety of ways, such as, as examples only, by heat welding, mechanical interference fit or gluing.

Leads 18 convey electrical stimuli and or sensing signals between the stimulus generator and the electrodes. Leads 18 and may also be used to properly position and anchor the electrodes with respect to each other and with respect to the preselected stimulation site. Leads 18 can be fabricated from an electrically conductive material such as a metallic or semi-metallic material and can be at least partially insulated with an electrically non-conductive material.

Figure 15:
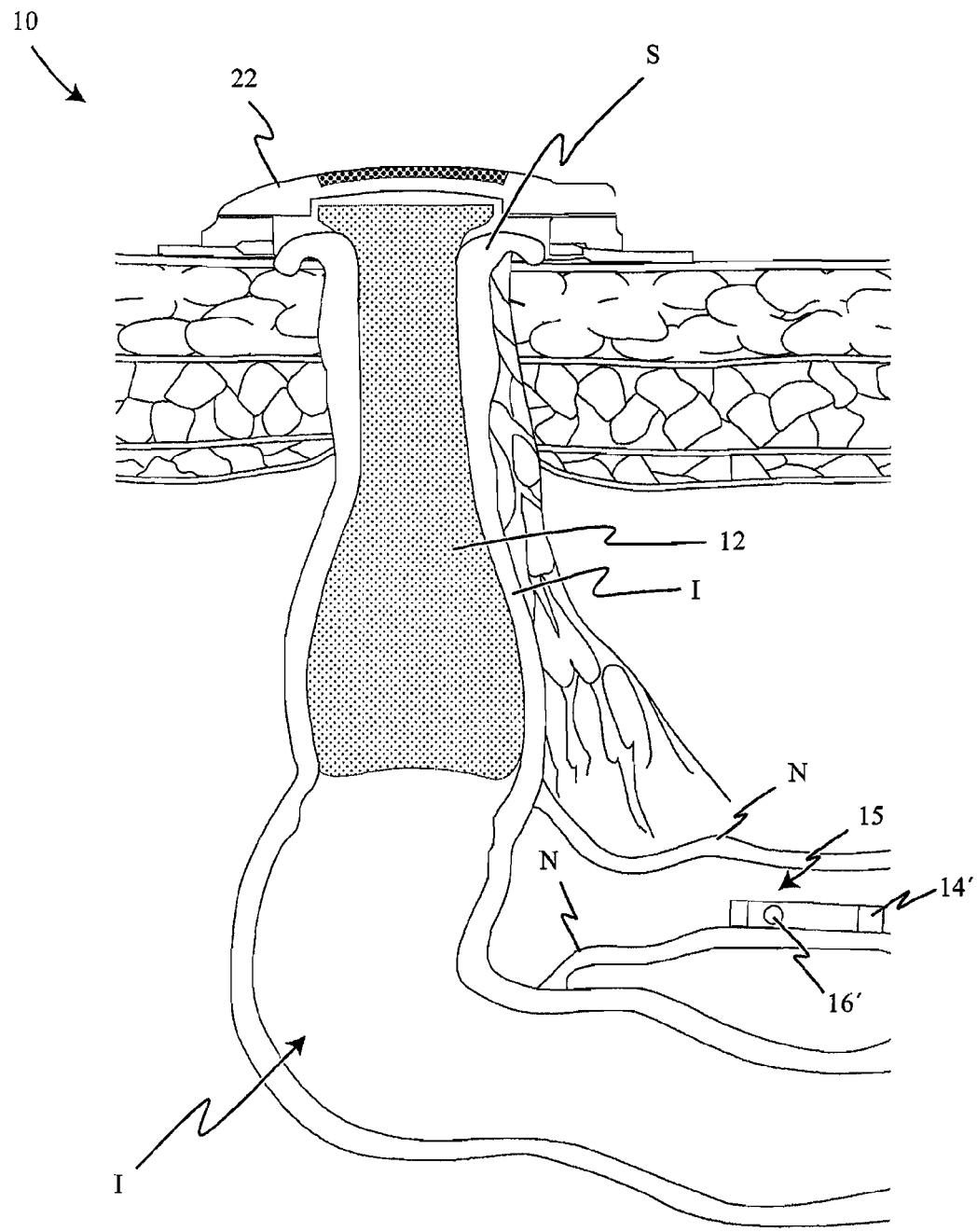
FIG. 15 is a longitudinal sectional view of an apparatus for providing continence, shown in place in an ostomy, the apparatus being constructed in accordance with and embodying the present invention and showing a plug type sealing device and an implantable stimulus generator, and being remotely operable via leadless stimulus generator electrodes fixed to large branch nerves N of the autonomic nervous system of the patient.
Figure 16:
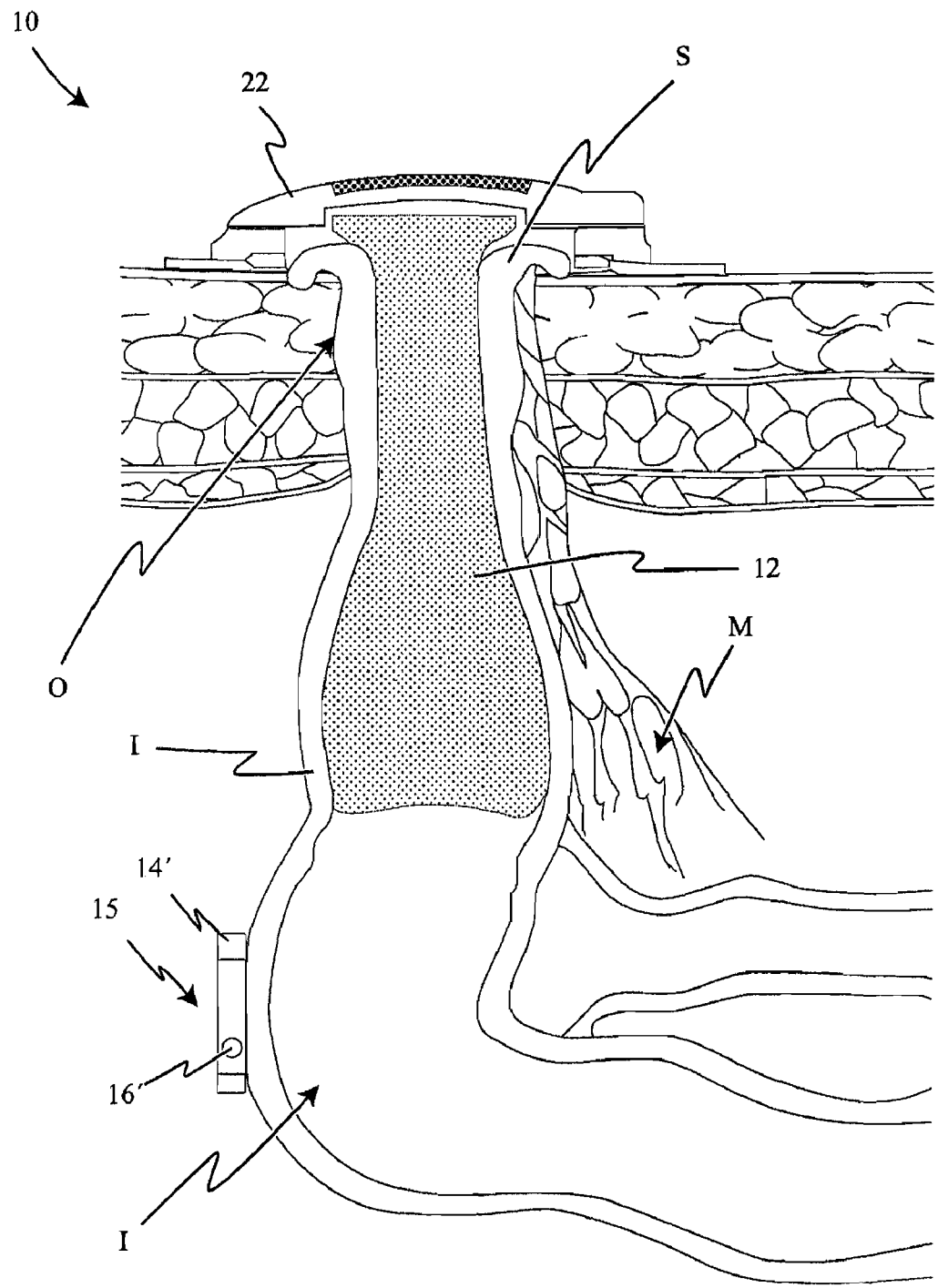
FIG. 16 is a longitudinal sectional view of an apparatus for providing continence, shown in place in an ostomy, the apparatus being constructed in accordance with and embodying the present invention and showing a plug type sealing device and a implantable stimulus generator, and being remotely operable via leadless stimulus generator electrodes fixed extraluminally to the intestinal wall.
Figure 17:
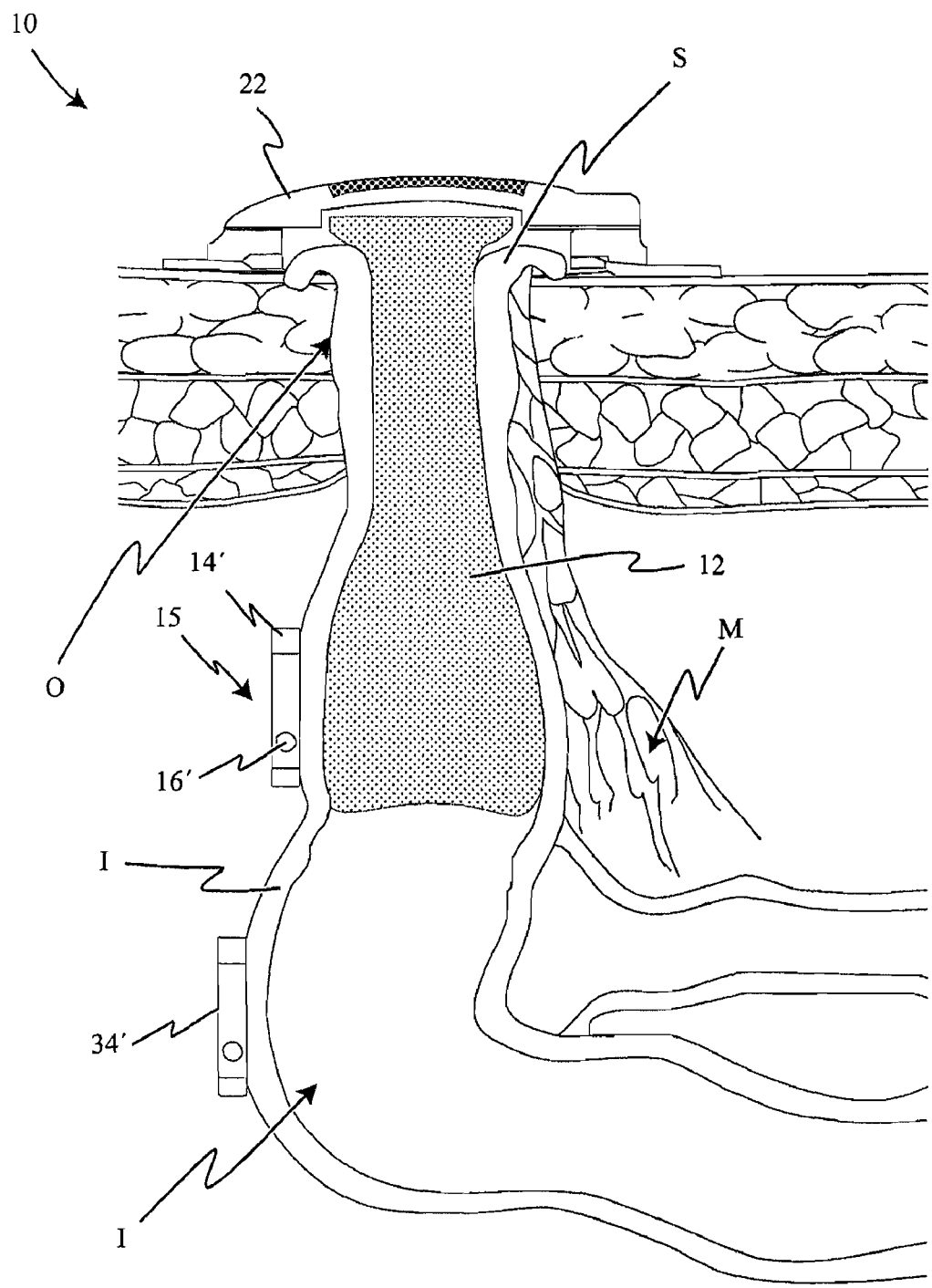
FIG. 17 is a longitudinal sectional view of an apparatus for providing continence, shown in place in an ostomy, the apparatus being constructed in accordance with and embodying the present invention and showing a plug type sealing device and a implantable stimulus generator, and being remotely operable via leadless stimulus generator electrodes fixed extraluminally to the intestinal wall, and a implantable sensing device for communicating sensed information to the leadless stimulus generator.

Another embodiment of apparatus 10, such as that illustrated in FIGS. 15, 16 and 17 for example, includes a leadless configuration, where an implanted stimulus generator 14' and at least one pair of electrodes 16' can be combined into a single package 15, as shown. Alternatively, the implanted stimulus generator 14' and at least one pair of electrodes 16' can be separate and are not integrated into a single package. In either configuration, the implantable device is sufficiently small to permit placement thereof adjacent to, or in contact with, the tissue to be stimulated and/or sensed. This configuration also allows stimulus generator 14' to be implanted with relative ease and rapidity (e.g., using endoscopic or laparoscopic techniques) and minimizes the distance traversed and the surgical planes crossed by stimulus generator 14', to minimize surgical risks. In a configuration using a single package 15, the device 15 may operate independently, or in a coordinated manner with other implanted devices, or with external devices. For example, the device 15 may incorporate a structure for sensing an electrical, physical, or chemical event or status, which it may then use to control stimulation parameters in a closed loop system. The sensing 16' and stimulating structures 14' may be incorporated into a single device, i.e. a unitary sensing/stimulating package 15, or a separate sensing device 34 may communicate sensed information to at least one device 15 with stimulating structure 14', as shown in FIG. 17.

Figure 8:
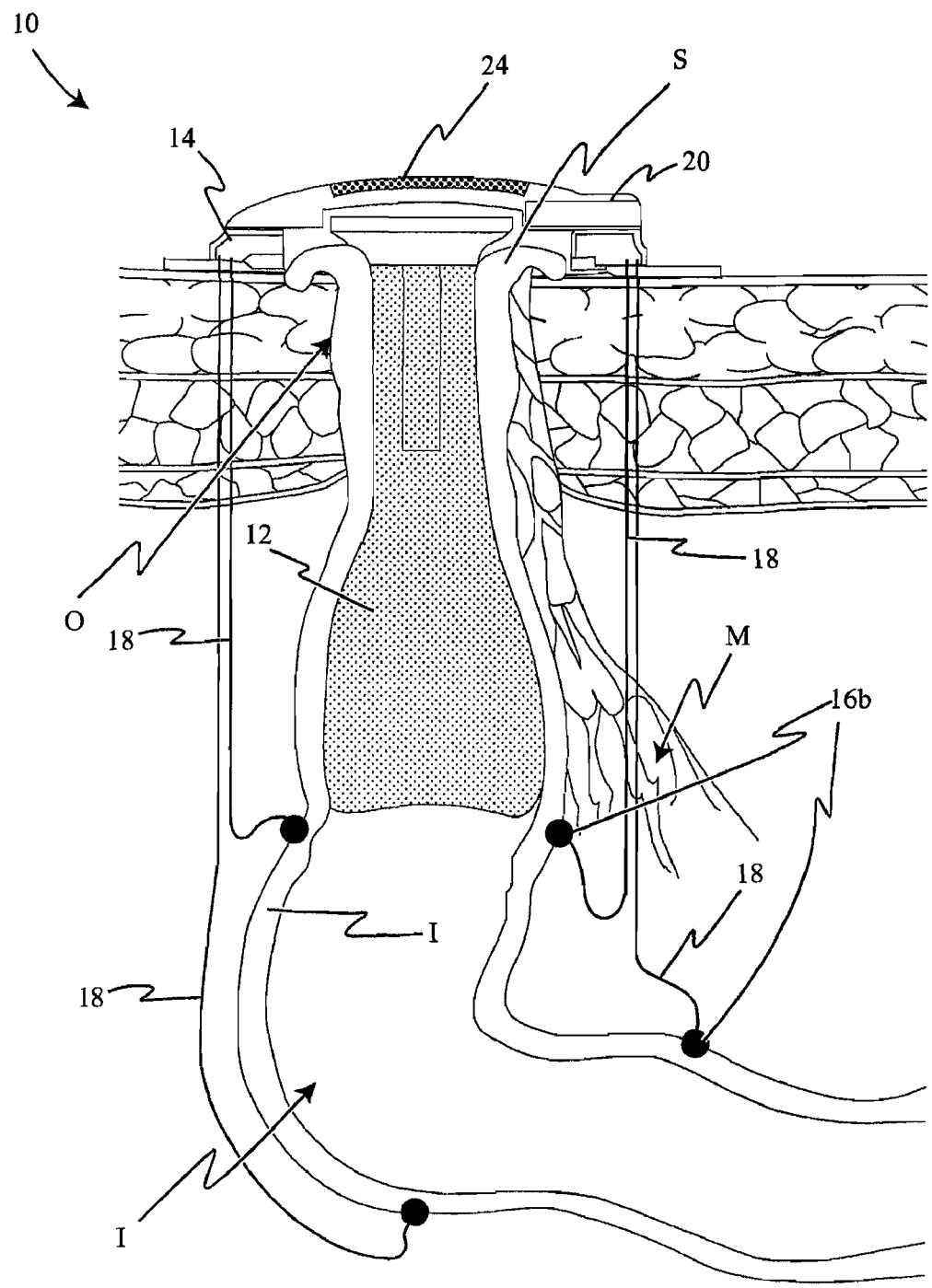
FIG. 8 is a longitudinal sectional view of an apparatus for providing continence in keeping with the embodiment of FIG. 5, but having the electrodes fixed at different sites.
Figure 9:
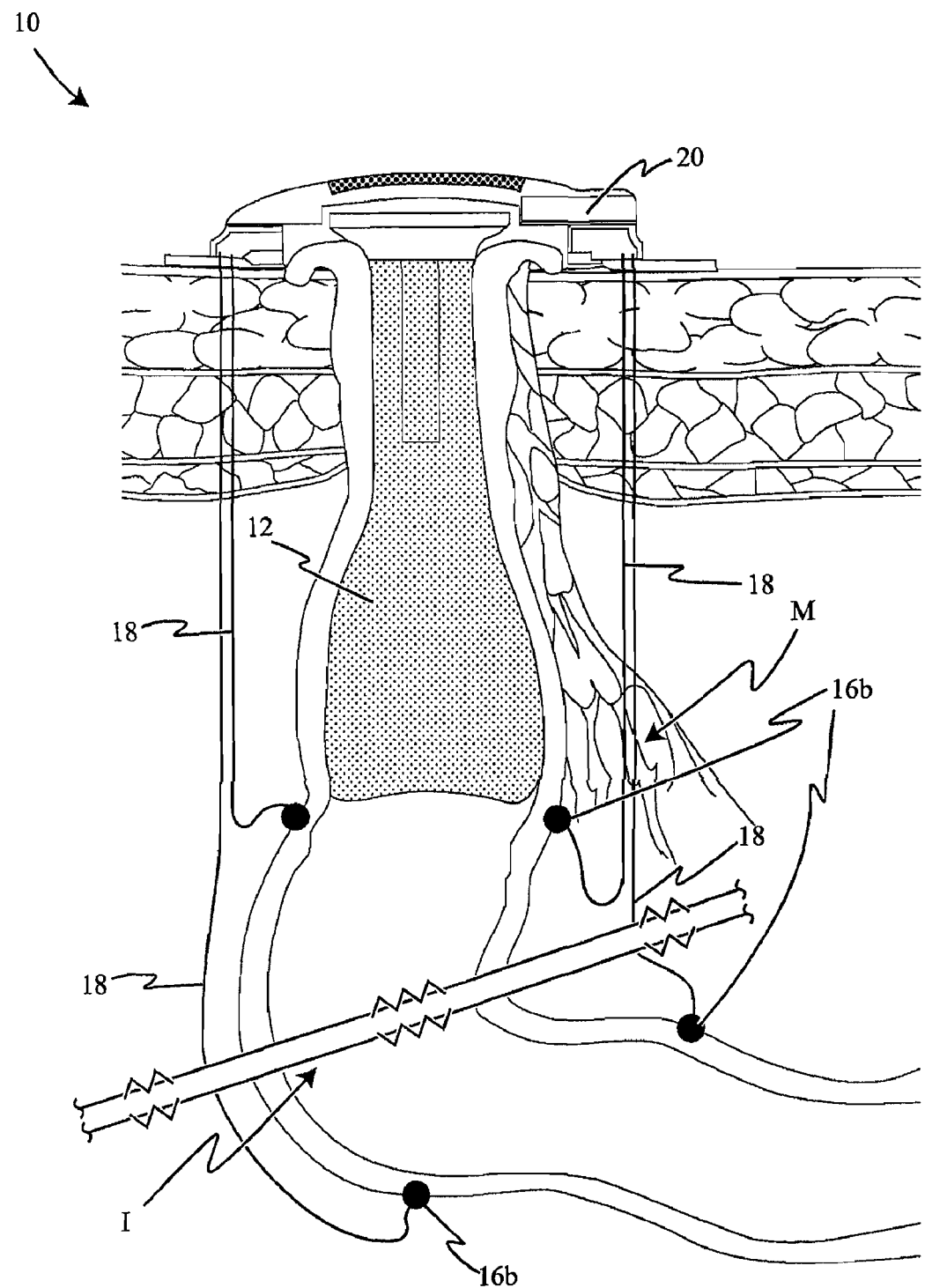
FIG. 9 is a longitudinal sectional view of an apparatus for providing continence, in keeping with the embodiment of FIG. 5, but having the electrodes fixed adjacent to and remotely from the sealing device.
Figure 10:
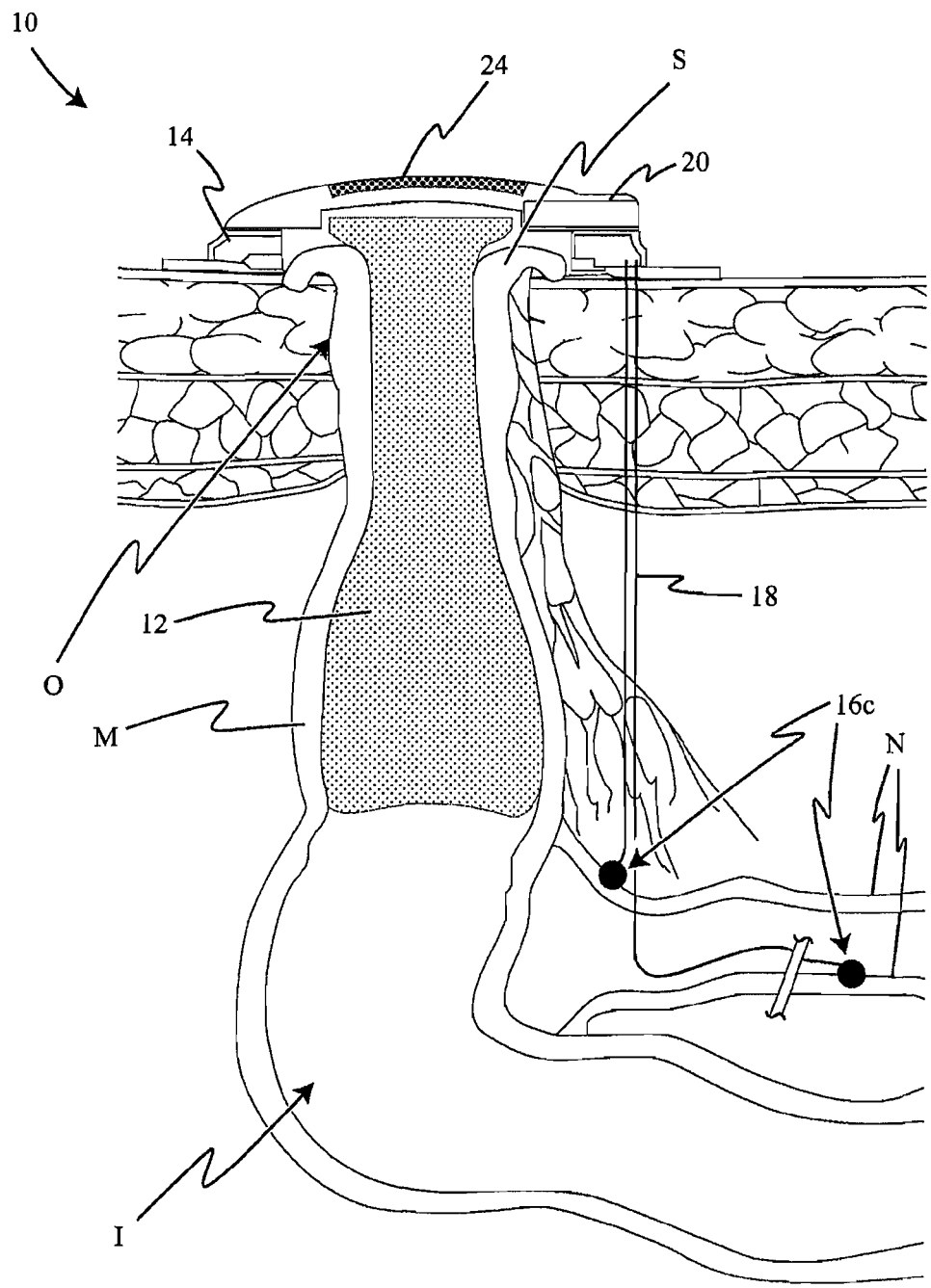
FIG. 10 is a longitudinal sectional view of an apparatus for providing continence, shown in place in an ostomy, the apparatus being constructed in accordance with and embodying the present invention and showing a plug type sealing device and an external stimulus generator positioned peristomally and having electrodes connected thereto, the electrodes being fixed to large branch nerves N of the autonomic nervous system of the patient.
Figure 11:
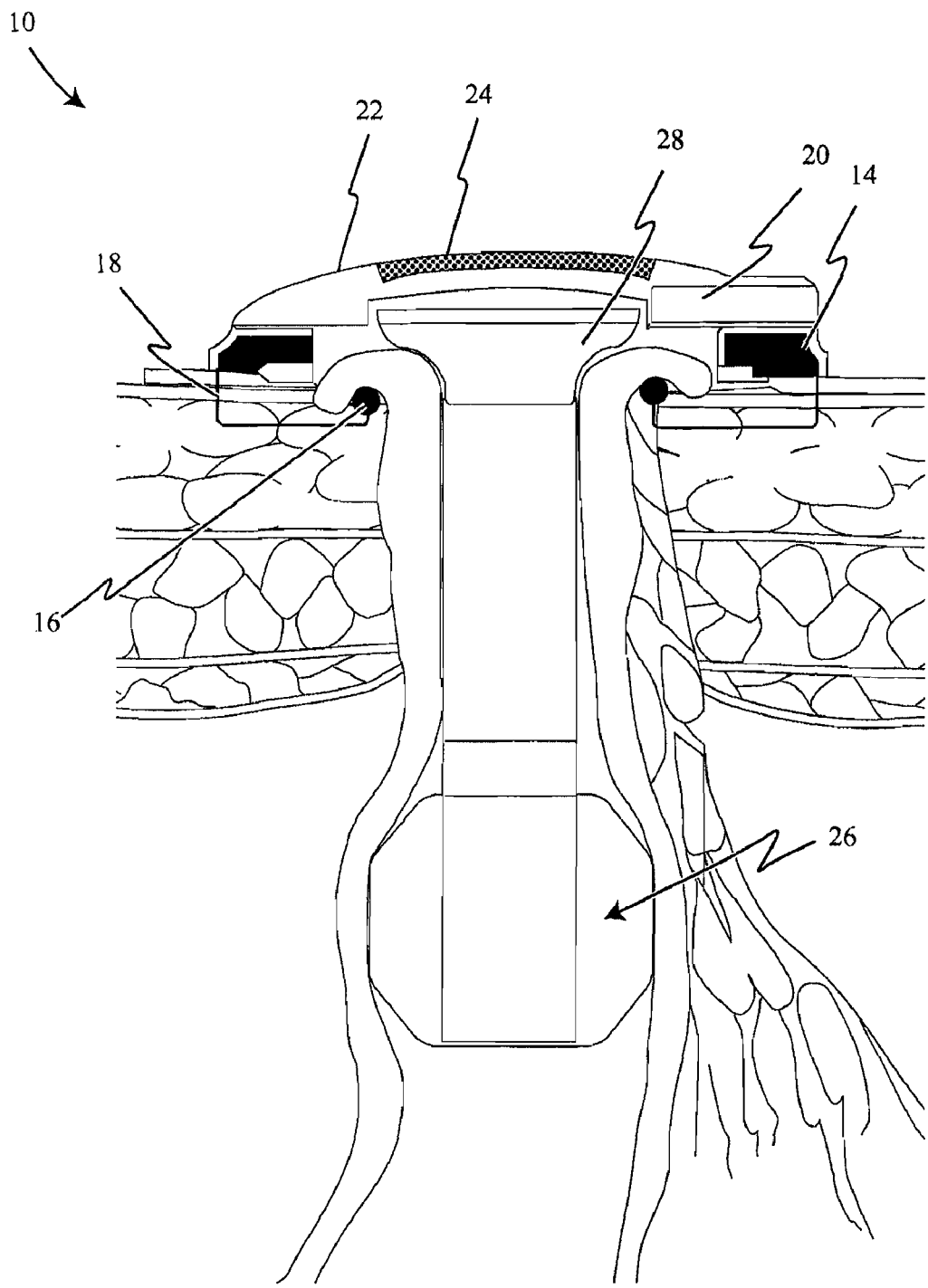
FIG. 11 is a longitudinal sectional view of an apparatus for providing continence, shown in place in an ostomy, the apparatus being constructed in accordance with and embodying the present invention and showing a catheter and plug type sealing device and an external stimulus generator positioned peristomally and having electrodes connected thereto, the electrodes being fixed extraluminally to the intestinal wall.
Figure 12:
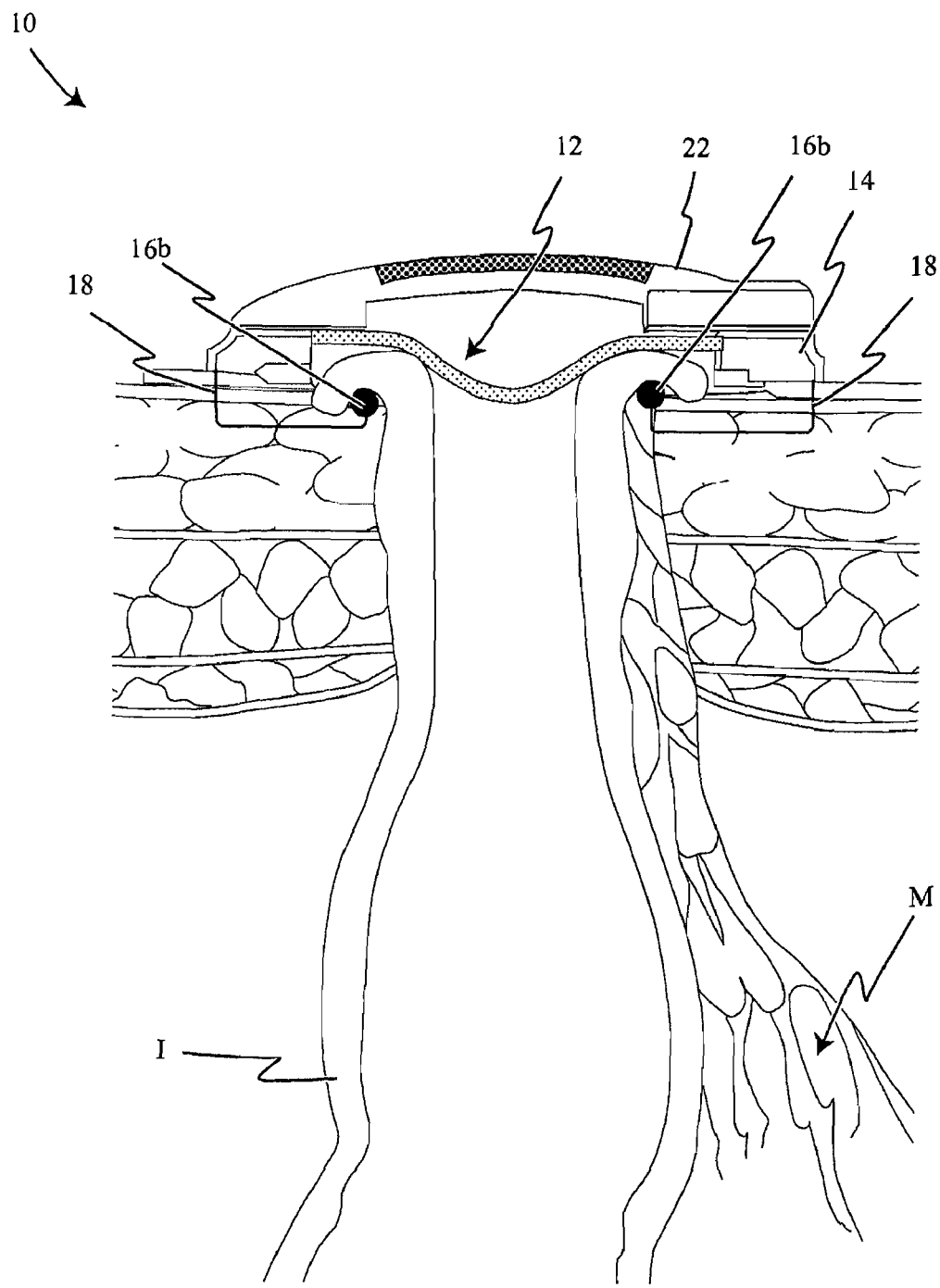
FIG. 12 is a longitudinal sectional view of an apparatus for providing continence, shown in place in an ostomy, the apparatus being constructed in accordance with and embodying the present invention and showing a stoma sealing membrane type sealing device and an external stimulus generator positioned peristomally and having electrodes connected thereto, the electrodes being fixed extraluminally to the intestinal wall.

Apparatus 10 can also electrically stimulate and/or sense segments of the intestine other than the segment being sealed—FIGS. 8 and 9. For example, if the segment of the intestine being sealed is the stoma, then apparatus 10 can also electrically stimulate and/or sense a segment of muscle proximal to sealing structure 12, in order to arrest the advancement of intestinal contents (stool) toward stoma S, for example.

Also provided in accordance with an embodiment of the present invention is a method for controlling evacuation of stool from the ostomy including; applying additional electrical stimuli to a target segment of intestinal muscles when evacuation from that segment of intestine is desired. If desired, the electrical stimuli can be provided sequentially, in a proximal to distal direction, in order to initiate, enhance, mimic or produce peristalsis in the target segment of the intestine, in a proximal to distal direction. Sealing structure 10 can be removed manually prior to initiation of peristaltic action, or the peristaltic action can be employed to facilitate expulsion of the sealing structure from ostomy O.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An apparatus for providing continence to a gastrointestinal ostomy of a patient, comprising:
    a sealing device for retaining discharge of effluents or waste products from the ostomy;
    at least one pair of electrodes capable of delivering electrical stimulation; and
    at least one stimulation generator in selective communication with the at least one pair of electrodes;
    wherein the at least one stimulation generator provides through any of the at least one pair of electrodes electrical stimulation to the patient's intestine, to thereby inhibit the advancement of intestinal contents by controlling muscle activity in a segment of the intestine.

2. The apparatus of claim 1, wherein the sealing device is selected from the group consisting of a plug, a catheter with removable plug, a stoma sealing membrane, an absorbent tampon, and an absorbent pad.

3. The apparatus of claim 1, wherein the sealing device is an ostomy bag.

4. The apparatus of claim 1, wherein the sealing device further comprises a vent to permit release of flatus via the ostomy.

5. The apparatus of claim 1, and further comprising at least one electrical lead to provide electrical communication between the stimulus generator and the at least one pair of electrodes.

6. The apparatus of claim 1, wherein at least one of the at least one pair of electrodes can be attached during use directly to the smooth muscle of the patient's intestine, to thereby deliver electrical stimulation directly to smooth muscles of the patient's intestine.

7. The apparatus of claim 1, wherein at least one of the at least one pair of electrodes can be disposed during use to deliver electrical stimulation directly to portions of the patient's enteric nervous system.

8. The apparatus of claim 1, wherein at least one of the at least one pair of electrodes can be disposed during use to deliver stimulation directly to larger branch nerves of the autonomic nervous system associated with the smooth muscles of the patient's intestine.

9. The apparatus of claim 1, wherein the stimulus generator has circuitry for providing at least one electrical stimulation pulse.

10. The apparatus of claim 1, wherein the stimulus generator has circuitry for providing multiple electrical stimuli in a preselected order.

11. The apparatus of claim 1, wherein the stimulus generator has circuitry for controlling all electrical stimulation pulse parameters.

12. The apparatus of claim 1, wherein the stimulus generator has circuitry for sensing at least one of electrical, physical, and chemical activity in the patient's intestine.

13. The apparatus of claim 1, wherein at least one of the at least one pairs of electrodes is incorporated into the material of the sealing device.

14. The apparatus of claim 1, wherein at least one of the at least one pairs of electrodes is located at least one of distal and proximal to the sealing device.

15. The apparatus of claim 1, and further comprising a cover, mountable over a distal end of the patient's ostomy and wherein the stimulation generator is mounted beneath the ostomy cover.

16. The apparatus of claim 1, wherein the at least one pair of electrodes and the at least one stimulation generator are combined together to provide a unitary sensing/stimulating package.

17. The apparatus of claim 16, and further comprising at least one separate sensing device not combined with a stimulation generator, so that the apparatus includes both a separate sensing device and a unitary sensing/stimulating package.

18. A method for providing continence to a gastrointestinal ostomy of a patient; comprising the steps of:
    providing a patient having a gastrointestinal ostomy with an apparatus for providing continence, the apparatus having a sealing device for retaining discharge of effluents or waste products from the ostomy, at least one pair of electrodes capable of delivering electrical stimulation, at least one stimulation generator providing electrical stimulation to the patient's intestine through any of the at least one pair of electrodes;
    preselecting any of the at least one pairs of electrodes and the site of the electrical stimulation; and
    applying electrical stimulation via the stimulation generator to the preselected at least one pairs of electrodes;
    thereby inhibiting advancement of intestinal contents by controlling muscle activity in a segment of the intestine.

19. The method of claim 18, and further comprising inducing at least one of contraction and relaxation of the smooth muscles of the patient's intestine by electrical stimulation.

20. The method of claim 18, and further comprising inducing at least one of a tonic state and a flaccid state in the smooth muscles of the patient's intestine by electrical stimulation.

* * * * *